(12) United States Patent
Hadd et al.

(10) Patent No.: US 12,274,689 B2
(45) Date of Patent: Apr. 15, 2025

(54) COMPOUND FOR THE MANAGEMENT OF FELINE DIABETES

(71) Applicant: INCREVET, INC., Boston, MA (US)

(72) Inventors: Michael Hadd, San Jose, CA (US); Albert Collinson, Berlin, MA (US); Brian Seed, Boston, MA (US)

(73) Assignee: IncreVet, Inc., Framingham, MA (US)

( * ) Notice: Subject to any disclaimer, the term of this patent is extended or adjusted under 35 U.S.C. 154(b) by 766 days.

(21) Appl. No.: 16/818,026

(22) Filed: Mar. 13, 2020

(65) Prior Publication Data

US 2020/0289457 A1    Sep. 17, 2020

Related U.S. Application Data

(60) Provisional application No. 62/818,589, filed on Mar. 14, 2019.

(51) Int. Cl.
*A61K 31/351* (2006.01)
*A61P 3/10* (2006.01)

(52) U.S. Cl.
CPC .............. *A61K 31/351* (2013.01); *A61P 3/10* (2018.01)

(58) Field of Classification Search
None
See application file for complete search history.

(56) References Cited

U.S. PATENT DOCUMENTS

| | | |
|---|---|---|
| 6,410,063 B1 | 6/2002 | Jewell et al. |
| 7,838,499 B2 | 11/2010 | Chen et al. |
| 8,106,021 B2 | 1/2012 | Chen et al. |
| 8,283,454 B2 | 10/2012 | Liou et al. |
| 8,575,321 B2 | 11/2013 | Chen et al. |
| 8,802,637 B2 | 8/2014 | Chen et al. |
| 8,987,323 B2 | 3/2015 | Cai et al. |
| 9,006,403 B2 | 4/2015 | Liou et al. |
| 9,061,060 B2 | 6/2015 | Seed et al. |
| 9,834,573 B2 | 12/2017 | Cai et al. |
| 10,533,032 B2 | 1/2020 | Cai et al. |
| 10,981,942 B2 | 4/2021 | Cai et al. |
| 2012/0238510 A1 | 9/2012 | Cai et al. |
| 2012/0329732 A1 | 12/2012 | Chen et al. |
| 2015/0164856 A1 | 6/2015 | Reiche et al. |
| 2015/0320808 A1 | 11/2015 | Burcelin et al. |
| 2018/0000123 A1 | 1/2018 | Duclos et al. |
| 2019/0343853 A1 | 11/2019 | Mechanic et al. |
| 2020/0289457 A1 | 9/2020 | Hadd et al. |
| 2020/0352968 A1 | 11/2020 | Hadd et al. |
| 2022/0117898 A1 | 4/2022 | Wang et al. |
| 2023/0000816 A1 | 1/2023 | Hadd et al. |

FOREIGN PATENT DOCUMENTS

| | | |
|---|---|---|
| WO | WO-2020186142 A1 | 9/2020 |
| WO | WO-2021092341 A1 | 5/2021 |
| WO | WO-2022073151 A1 | 4/2022 |

OTHER PUBLICATIONS

Andrikopoulos et al., "Differential effect of in bred mouse strain (C57BL/6, DBA/2, 129T2) on insulin secretory function in response to a high fat diet", Journal of Endocrinology, 2005, vol. 187, pp. 45-53.
International Search Report for PCT/US2020/022567 mailed May 15, 2020, 3 pages.
Lukens et al., "Pituitary-diabetes in the CAT: Recovery Following Phlorhizin Treatment", Endocronolgy, Jun. 1943, vol. 32 pp. 475.
Lukens et al., "Steroid diabetes in the Cat Protection of the Islets by Insulin or Phlorhizin", Diabetes, May-Jun. 1961, vol. 10, No. 3, pp. 182-189.
Niessen et al., "Studying Cat (*Felis catus*) diabetes: Beware of the Acromegalic Imposter", PLOS One, May 29, 2015, 18 pages.
Rucinsky et al., "AAHA diabetes management Guidelines for Dogs and Cats", Journal of the American Animal Hospital Association, My/Jun. 2010, vol. 46, pp. 215-224.
Scott-Moncrieff, "Insulin Resistance in Cats", Vet Clin Small Anim, 2010, vol. 40, pp. 241-257.
Sparkes et al., "ISFM Consensus Guidelines on the Practical Management of Diabetes Mellitus in Cats", Journal of Feline Medicine and Surgery, 2015, vol. 17, pp. 235-250.
Written Opinion for PCT/US2020/022567 mailed May 15, 2020, 9 pages.
Zhang et al., "EGT1442, a potent and selective SGLT2 inhibitor, attenuates blood glucose and HbA1c levels in db/db mice and prolongs the survival of stroke-prone rats", Pharmacological Research, 2011, vol. 63, pp. 284-293.
European Patent Office, Extended European Search Report for European Patent Application No. 20770420.6, mailed Nov. 15, 2022, 8 pages.

(Continued)

*Primary Examiner* — Po-Chih Chen
(74) *Attorney, Agent, or Firm* — McBee, Moore & Vanik IP, LLC

(57) ABSTRACT

Provided herein are methods of managing feline diabetes, said methods include administering to a feline in need thereof a total daily dosage of about 5 to 50 mg of Compound 1, having the formula:

(Compound 1)

or a pharmaceutically acceptable form thereof. Also provided herein are methods of managing feline diabetes by administering to a feline in need thereof an effective amount of a SGLT inhibitor, wherein said effective amount is no more than 10 to 30% of the dose required to produce an elevated frequency of diarrhea or loose stool in a healthy feline.

8 Claims, 10 Drawing Sheets

(56) References Cited

OTHER PUBLICATIONS

U.S. Appl. No. 18/131,727, filed Apr. 6, 2023, Hadd et al.
U.S. Appl. No. 18/318,133, filed May 16, 2023, Li et al.
Benedict et al., Evaluation of bexagliflozin in cats with poorly regulated diabetes mellitus, The Canadian Journal of Veterinary Research, 2022, vol. 86, pp. 52-58.
Hadd et al., Safety and effectiveness of the sodium-glucose cotransporter inhibitor bexagliflozin in cats newly diagnosed with diabetes mellitus, Journal of Veterinary Internal Medicine, 2023, vol. 37, pp. 915-924.

| 2θ | d space (Å) | Intensity (%) |
| --- | --- | --- |
| 5.4 ± 0.1 | 16.509 ± 0.314 | 11 |
| 10.7 ± 0.1 | 8.255 ± 0.078 | 3 |
| 11.2 ± 0.1 | 7.922 ± 0.071 | 47 |
| 11.3 ± 0.1 | 7.817 ± 0.069 | 12 |
| 11.9 ± 0.1 | 7.445 ± 0.063 | 14 |
| 12.9 ± 0.1 | 6.886 ± 0.054 | 100 |
| 14.7 ± 0.1 | 6.035 ± 0.041 | 3 |
| 15.0 ± 0.1 | 5.908 ± 0.039 | 4 |
| 15.5 ± 0.1 | 5.700 ± 0.037 | 56 |
| 16.1 ± 0.1 | 5.494 ± 0.034 | 5 |
| 16.3 ± 0.1 | 5.438 ± 0.033 | 32 |
| 17.8 ± 0.1 | 4.982 ± 0.028 | 75 |
| 18.7 ± 0.1 | 4.744 ± 0.025 | 9 |
| 19.1 ± 0.1 | 4.641 ± 0.024 | 92 |
| 20.0 ± 0.1 | 4.430 ± 0.022 | 50 |
| 20.6 ± 0.1 | 4.320 ± 0.021 | 41 |
| 20.7 ± 0.1 | 4.282 ± 0.021 | 76 |
| 21.2 ± 0.1 | 4.182 ± 0.020 | 35 |
| 21.6 ± 0.1 | 4.121 ± 0.019 | 6 |
| 22.4 ± 0.1 | 3.963 ± 0.018 | 8 |
| 22.8 ± 0.1 | 3.903 ± 0.017 | 42 |
| 23.0 ± 0.1 | 3.870 ± 0.017 | 24 |
| 23.4 ± 0.1 | 3.810 ± 0.016 | 20 |
| 23.6 ± 0.1 | 3.770 ± 0.016 | 29 |
| 23.9 ± 0.1 | 3.725 ± 0.015 | 34 |
| 24.7 ± 0.1 | 3.604 ± 0.014 | 12 |
| 24.9 ± 0.1 | 3.570 ± 0.014 | 9 |
| 25.4 ± 0.1 | 3.506 ± 0.014 | 12 |
| 25.8 ± 0.1 | 3.450 ± 0.013 | 23 |
| 27.0 ± 0.1 | 3.299 ± 0.012 | 2 |
| 27.5 ± 0.1 | 3.240 ± 0.012 | 9 |
| 27.8 ± 0.1 | 3.208 ± 0.011 | 14 |
| 28.2 ± 0.1 | 3.159 ± 0.011 | 13 |
| 28.9 ± 0.1 | 3.090 ± 0.010 | 5 |
| 29.0 ± 0.1 | 3.074 ± 0.010 | 3 |
| 29.6 ± 0.1 | 3.020 ± 0.010 | 8 |

Raman peak list for crystalline (2S,3R,4R,5S,6R)-2-(4-chloro-3-(4-(2-cyclopropoxyethoxy)benzyl)phenyl)-6-(hydroxymethyl)tetrahydro-2*H*-pyran-3,4,5-triol (cm$^{-1}$)

| | |
|---|---|
| 144 | 1212 |
| 189 | 1229 |
| 216 | 1302 |
| 226 | 1323 |
| 284 | 1343 |
| 315 | 1380 |
| 353 | |
| 387 | |
| 419 | |
| 432 | |
| 449 | |
| 503 | |
| 530 | |
| 565 | |
| 594 | |
| 638 | |
| 688 | |
| 716 | |
| 728 | |
| 755 | |
| 790 | |
| 825 | |
| 850 | |
| 884 | |
| 901 | |
| 919 | |
| 934 | |
| 974 | |
| 984 | |
| 1014 | |
| 1030 | |
| 1052 | |
| 1070 | |
| 1120 | |
| 1134 | |
| 1178 | |
| 1205 | |

COMPOUND FOR THE MANAGEMENT OF FELINE DIABETES

CROSS-REFERENCES TO RELATED APPLICATIONS

This application claims priority to U.S. Provisional Application No. 62/818,589, filed Mar. 14, 2019, which is incorporated by reference in its entirety and for all purposes.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Diabetes mellitus is a disease characterized by a sustained high blood glucose concentration (hyperglycemia) that adversely affects multiple organ systems and in severe cases can result in death. Diabetes has been observed in companion animals such as cats, dogs and horses as well as humans. As in human populations, diabetes in cats is an increasing health problem, and is associated with both advancing age and obesity.

In veterinary medicine, the objectives of a therapy take into consideration the perceptions and needs of the owner or person responsible for the care of an animal. A strategy for disease treatment that increases the objective health of the animal but that has adverse consequences on the owner, for example to increase owner anxiety over the health of the animal, would be considered inferior to a strategy that has less objective efficacy but decreases the owner's anxiety. As a result, veterinary objectives emphasize disease management, distinguished from simple disease treatment.

There are two major types of diabetes mellitus in humans: Type 1 (T1DM), also known as insulin dependent diabetes (IDDM) and Type 2 (T2DM), also known as insulin independent or non-insulin dependent diabetes (NIDDM).

Type 1 diabetes results from a failure of the body to produce insulin, most often due to a loss of the endocrine cells known as β cells, which in many organisms are found in clusters, called islets, within the exocrine pancreas. Type 2 diabetes is a disease of insulin resistance, in which the islet β cells are capable of producing insulin, but the tissues responsible for taking up glucose from the blood do not respond adequately to the insulin that is produced. Over the course of sustained T2DM, β cells may become less capable of producing insulin, and/or may succumb to the stress of constant high insulin production. In such a setting exogenous insulin may be required to maintain normal glucose levels (euglycemia or normoglycemia). However, a risk of administration of too much insulin is hypoglycemia, which can result in coma and death.

Insulin lowers the concentration of glucose in the blood by stimulating the uptake and metabolism of glucose by liver, muscle and adipose tissue. Insulin stimulates the storage of glucose in the liver and muscles as glycogen, and in adipose tissue as triglycerides. Insulin also promotes the utilization of glucose in muscle for energy. Thus, insufficient insulin levels in the blood, or decreased sensitivity to insulin, gives rise to excessively high levels of glucose in the blood. When the glucose concentration in the blood rises above a certain critical level, called the renal threshold for glucosuria, glucose begins to appear in the urine. Prior to the advent of reliable blood-based tests for diabetes, the appearance of glucose in urine was often the first indication of the disease.

Under normal conditions the kidneys allow low molecular weight compounds, including glucose, in the blood to exit the body in the glomerular filtrate. From the filtrate, the kidneys selectively recover nearly all of the water, sodium, potassium and chloride ions, as well as important metabolites including vitamins, glucose and other sugars, and amino acids. The energetically expensive process of discarding nearly the entire contents of plasma, then selectively reabsorbing only those components of interest, underlies the ability of the kidney to discharge toxins of great and unpredictable diversity. The mechanism for reabsorption of glucose also provides a homeostatic capability when plasma glucose levels rise too high. When the concentration of glucose in the blood exceeds the renal threshold for glucosuria, some of the excess glucose is discharged in the urine, palliating to some extent the adverse consequences of elevated plasma glucose.

As the degree of glucosuria rises, an increase in urinary output is observed, the consequence of a phenomenon known as osmotic diuresis. Glucose in the filtrate osmotically prevents the concentration of urine by water reabsorption, leading to a higher rate of loss of water, in turn resulting in dehydration. Dehydration causes increased thirst and water consumption. The inability to utilize glucose energy eventually leads to weight loss despite an increase in appetite. Excessive water consumption (polydipsia), food consumption (polyphagia or hyperphagia) and urine production (polyuria) are common symptoms of advanced diabetes.

The toxic effects of excess plasma levels of glucose include the non-enzymatic (spontaneous) glycosylation of cells and tissues. Glycosylated products accumulate in tissues and may eventually form cross-linked proteins, which are termed advanced glycation end products. Although the detailed mechanisms are for the most part unknown, it is well understood that diabetes elevates the likelihood or severity of several conditions and can result in painful neuropathies, impaired circulation, gangrene, amputation, renal failure, blindness, myocardial infarction and stroke.

The determination of the degree of overall glycemic control is an important element of a diabetes management plan. Measurement of serum glucose by an analytical laboratory, or of blood glucose with a point-of-care device such as a home glucometer, can aid in assessing glycemic status. Glucometers measure glucose in whole blood, whereas analytical laboratories typically measure glucose in serum, the liquid phase resulting from blood coagulation. Individual serum or blood glucose values can vary substantially throughout the day, typically rising after meals and falling after prolonged fasting. Such daily fluctuations can reduce the utility of serum or blood sampling for determining the degree of glycemic control resulting from a given therapeutic intervention.

To provide a better assessment of the degree of control of feline diabetes, it is common to take multiple blood samples over the course of a day, typically as an inpatient study in which the cat is housed in a veterinary clinic for the duration of the measurements. The resulting profiles of blood glucose as a function of time are known as blood glucose curves, and are often conducted to confirm an initial diagnosis, or assess the effectiveness of a management plan.

Confinement of a cat in a veterinary clinic can be stressful to a cat, and one of the documented consequences of stress is hyperglycemia. Hence blood glucose curves obtained in a clinic, although rarely confounded by technical limitations affecting the blood draw or measurement accuracy, can consist of unreliably high values that reflect the action of cortisol, the principal hormone released in stress, and not the natural course of fluctuation of the cat's daily blood glucose concentration. Hence measurements in the clinic always need to be evaluated for their potential to underestimate the degree of glycemic control.

According to guidelines published by the International Society for Feline Medicine (Sparkes et al., 2015; J Feline Med Surg 17:235), the primary goal of management of feline diabetes, as measured by blood glucose curve criteria, is to maintain the blood glucose between a peak of 10-14 mmol/L (180-252 mg $dL^{-1}$) and a nadir of 4.5-8.0 mmol/L (80-144 mg $dL^{-1}$). Both peak and nadir are specified because the only approved medication for diabetes is insulin, which if administered in excess can cause a dangerous hypoglycemia. According to this guideline, a cat with diabetes is adequately managed if its blood glucose curve measurements fall between 80 and 252 mg $dL^{-1}$.

Related guidelines published by the American Animal Hospital Association (Rucinsky et al., 2010 J Am Anim Hosp Assoc 46:215) recommend the conduct of an at-home blood glucose curve having a target for average blood glucose of less than 250 mg $dL^{-1}$ with no single blood glucose measurement greater than 300 mg $dL^{-1}$ and a nadir of 80-150 mg $dL^{-1}$.

Blood glucose curves are inconvenient and expensive to conduct. As an alternative, surrogate measures of glycemic control that reflect the average blood glucose concentration over a long period of time, such as weeks to months, and that can be measured in a single blood sample, can be deployed.

In humans non-enzymatically glycated hemoglobin provides a convenient method to determine long term glycemic control. The N-terminal valine residues of hemoglobin A1 undergo a spontaneous chemical reaction with reducing sugars, of which glucose is the most abundant in the blood. The initial step is the formation of an enamine (Schiff base) between the glucose aldehyde tautomer and the N-terminal amino group. The second step, called an Amadori rearrangement, results in a tautomerization to produce a β-keto amine, often referred to as an Amadori adduct. Because the average lifetime of a human red blood cell is about 120 days, the degree of non-enzymatic glucosylation represents the average accumulation of glycation products over a mean period of half this time. Measurement of the fraction of glycated hemoglobin is the basis of an assay referred to as the hemoglobulin $A_{1c}$ ($HbA_{1c}$) assay. A sample of blood in which the percentage of $HbA_{1c}$ is less than 6.5 is typically considered to reflect good or adequate glycemic control, whereas higher percentages are typically interpreted as indicating the presence of diabetes.

The erythrocytes of cats have shorter half-lives than human erythrocytes, and the $HbA_{1c}$ levels are much lower, and less precisely measured. Instead, the preferred measure of sustained glycemic status in cats is the serum fructosamine assay, which also measures the non-enzymatic adducts created by the reaction of reducing sugars with primary amines. Mechanistically, these adducts are formed by the same reaction sequence as with the N-terminal amino group of hemoglobin, but can form on the ε-amino side chains of lysine, forming, in the case of glucose, a structure known as fructoselysine. The fructosamine test measures total serum keto amines by reversing the Amadori rearrangement. Under alkaline conditions, the Amadori products revert to the original enamines, which reduce nitroblue tetrazolium to a colored formazan dye that is quantitated spectrophotometrically at 540 nm. The fructosamine assay measures total 0-keto amines, but the largest component is that attributable to serum albumin, the most abundant protein in plasma. Albumin has a half-life of approximately 20 days, so the fructosamine measurement effectively measures the three-week history of glycemic control.

According to guidelines published by the International Society for Feline Medicine (Sparkes et al., 2015; J Feline Med Surg 17:235), a serum fructosamine level of less than 350 µmol $L^{-1}$ indicates either excellent glycemic control, insulin overdose or diabetic remission; of 350-450 µmol $L^{-1}$ indicates good glycemic control; of 450-550 µmol $L^{-1}$ indicates moderate glycemic control; and of >550 µmol $L^{-1}$ indicates poor glycemic control. These value ranges are predicated on testing laboratory methodology that places the upper limit of normal for serum fructosamine at approximately 350 µmol $L^{-1}$.

At present there are no approved oral hypoglycemic agents for the management of diabetes in cats. The standard of care for feline diabetes requires twice daily injections of insulin, titrated to desired effect. Cats show substantial inter-individual variation in insulin sensitivity and must be carefully observed to ensure that a fatal or neurologically catastrophic hypoglycemia does not occur. Although the administration of insulin can help control diabetes and slow disease progression, providing the proper dose and timing of the insulin can be challenging. For example, it is recommended that the administration of insulin be timed around a meal, but consistent timing of insulin with meals can be difficult to arrange and often results in a lower level of compliance.

As such, there is a need in the art for improved methods and compositions for reducing the hyperglycemia of feline diabetes and the hyperglycemia-associated clinical signs, and particularly for methods that do not entail injections and that do not require careful dose adjustment to preserve the wellbeing of the cat. The present disclosure addresses this need and provides related advantages. In particular the disclosure provides methods and compositions for the management of feline diabetes that comprise compounds that inhibit the glucose transport proteins known as SGLT1 and SGLT2.

Much of what is known about these proteins comes from studies of rodents and humans and is not necessarily applicable to cats. Cats are obligate carnivores and ordinarily consume very little carbohydrate. Cats lack receptors for sweet taste that are present in rodents and humans and the receptors and transporters responsible for carbohydrate sensing and movement cannot be assumed to function in the same manner as their cognates in rodents or humans. What follows, therefore, is an accounting of the general properties of carbohydrate transport as reflected by the largest body of current understanding, which may differ in material ways from the description of transport in cats.

Because glucose does not spontaneously diffuse across cell membranes, rodents and humans have two classes of integral membrane protein, called transporters, to facilitate the movement of glucose from the extracellular medium into the cell. One class, called 'equilibrative', does not favor the interior or the exterior, but rather allows glucose to move from the region of higher concentration to the region of lower (moving in the direction of equilibrium). Since cells consume glucose, this results in a net flux into the cell in most cases. The other class, called 'concentrative', relies on the natural gradient of sodium ions from the extracellular to the intracellular compartments. The gradient is sustained by active pumping of $Na^+$ by an energy-requiring (ATP-consuming) mechanism that exchanges intracellular $Na^+$ for extracellular $K^+$, thereby increasing the extracellular concentration of $Na^+$ and the intracellular concentration of $K^+$. Sodium-glucose linked transporters (SGLTs) transport one glucose and one $Na^+$ ion (in the case of SGLT2) or one glucose and two $Na^+$ ions (in the case of SGLT1) across the membrane in a single action. The $Na^+$ ions effectively carry the glucose with them into the cell. Concentrative transporters thus allow dilute extracellular glucose to be concentrated in the cell interior.

Most cells exhibit only equilibrative transport. The intestines and kidneys rely on concentrative transport to take up glucose from the diet or to retrieve glucose from urine. In the species studied to date SGLT1 is present in both intestine and kidney, whereas SGLT2 is found in the kidney, anatomically upstream of SGLT1 in the renal tubules. SGLT2 acquires glucose at a lower $Na^+$ cost than SGLT1, and under normal conditions is responsible for the reuptake of approximately 90% of the glucose in filtrate. In the absence of SGLT2, SGLT1 partially compensates, and 40-50% of the glucose is retained. The rest is lost to urine. Genetic deficiencies of SGLT2 are known in mice and humans and are generally benign, occult syndromes detected in humans only by random urine testing. Genetic deficiency of SGLT1 is a potentially lethal condition in humans, due to a severe diarrhea that can only be managed by strict dietary limitation of carbohydrate. Both SGLT1 and 2 cotransport large amounts of water with $Na^+$ and glucose. In humans and rodents, SGLT1 can transport both glucose and galactose. Whether galactose is a substrate for feline SGLT1 is presently not known.

Much of the early work on the physiology of renal reuptake of glucose was facilitated by the identification of a natural product, phlorizin, isolated from the bark of apple trees, that was eventually found to be an inhibitor of SGLT1 and SGLT2 in multiple species.

Phlorizin (also known in the literature as phloridzin, phloridizin, phlorhizin and phloridzine) was noted in the 19$^{th}$ century to promote glucosuria. At the time, because diabetes was characterized chiefly by the presence of glucose in urine, phlorizin was considered to be diabetogenic, and the early literature refers to "phlorizin diabetes." It was quickly recognized, however, that the glucosuria elicited by phlorizin resulted from a different mechanism than the glucosuria resulting from pancreatic damage or removal, and before the turn of the century, E. Hedon (Compt Rend Soc Biol 4:60 1897) reported the correction of experimental diabetes in dogs by the administration of phlorizin. A translation of his observations from French could be made as follows: "Another fact that, to my knowledge, has not been observed yet, is that when phloridzine is administered to pancreatectomized animals in full glycosuria, the hyperglycemia disappears; we see then an inverse relation between glycosuria and glucose; while the former is growing in a large proportion (as Minkowski has seen), the second decreases until it returns to the normal state." By the 1920s the action of phlorizin on the kidney had been elucidated and a comprehensive review of its actions had been published (Nash Physiol. Rev. 7: 385 1927).

A report of the use of phlorizin to reverse the hyperglycemia produced by experimental diabetes in cats was reported in 1943 by Lukens and coworkers (Lukens et al., Endocrinology 32:475 1943), and followed up by additional observations published in 1961 (Lukens et al., Diabetes 10:182 1961). The salutary effects of phlorizin on diabetes in cats included relief of stress on the pancreatic insulin-producing islet cells as well as a dramatic reduction of hyperglycemia. Lukens et al. demonstrated many effects that are considered characteristic of the action of a hypoglycemic agent on diabetic cats. They showed, for example, that phlorizin could protect animals from the development of diabetes, could restore normal glucose tolerance to diabetic animals, and could prevent exhaustion of the islets of Langerhans in the presence of experimental diabetes (Lukens et al., 1943, 1961). A key element of the studies made by Lukens and coworkers was the administration of phlorizin by subcutaneous injection of a suspension of the compound in olive oil. This effectively served as a sustained release depot formulation that delivered the active agent over a period of days. Without this strategy it is likely that their results could not have been attained. An O-glucoside, phlorizin is susceptible to the metabolic action of β-glucosidases and has a short half-life in most species.

Recently US 2015/0164856A1 has taught the use of one or more SGLT2 inhibitors to treat diabetes in feline animals. The publication teaches the uses of SGLT2 inhibitors are various, and can, for example, prevent the loss of pancreatic beta cell mass or prevent beta cell degeneration, prevent or treat diabetes, and treat a wide variety of diabetes-related ailments or conditions. US 2015/0164856A1 can be distinguished from the very similar demonstrations and assertions of Lukens and coworkers by the emphasis on SGLT2 inhibition. Phlorizin, as a mixed SGLT1/2 inhibitor in most species, has effects on two transporters, whereas US 2015/0164856A1 teaches inhibition solely of SGLT2. Indeed, US 2015/0164856A1 makes no mention of SGLT1. It is also worth noting that the selectivity of phlorizin for feline SGLT1 and SGLT2 is not presently known, nor is the relative contribution of the two transporters to renal reuptake of glucose in the cat.

US 2015/0164856A1 also does not disclose that, as is well known in the art, prediction of the actions of a compound in one species based on experience in another is one of the most hazardous prognostications in drug development. Due to evolutionary variation in the structure of target proteins, it is quite difficult to predict actions across species with any precision. Moreover species-dependent off-target effects are well known in the art. The rate and type of metabolism of xenobiotics are important determinants of drug exposure, and are known to exhibit great variability from one species to another. In part, this is likely due to the strong genetic selection that is applied to xenobiotic metabolism pathways, which allow some species to consume food sources that are otherwise toxic to other species.

BRIEF SUMMARY OF THE INVENTION

Provided herein are methods of managing feline diabetes; said methods include administering to a feline in need thereof a total daily dosage of about 5 to 50 mg of Compound 1, (bexagliflozin), having the formula:

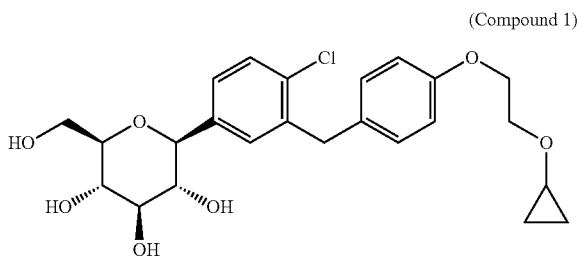 [SMILES: OC[C@H]1O[C@@H](c2ccc(Cl)c(Cc3ccc(OCCOC4CC4)cc3)c2)[C@H](O)[C@@H](O)[C@@H]1O]

(Compound 1)

or a pharmaceutically acceptable form thereof.

Other objects, features, and advantages of the present invention will be apparent to one of skill in the art from the following detailed description and figures.

BRIEF DESCRIPTION OF THE DRAWINGS

FIG. 2 provides a Table of XRPD data for the XRPD spectra in FIG. 1.

FIG. 4 provides a Raman peak list for the Raman spectra in FIG. 1.

DETAILED DESCRIPTION OF THE INVENTION

I. General

Figure 1:
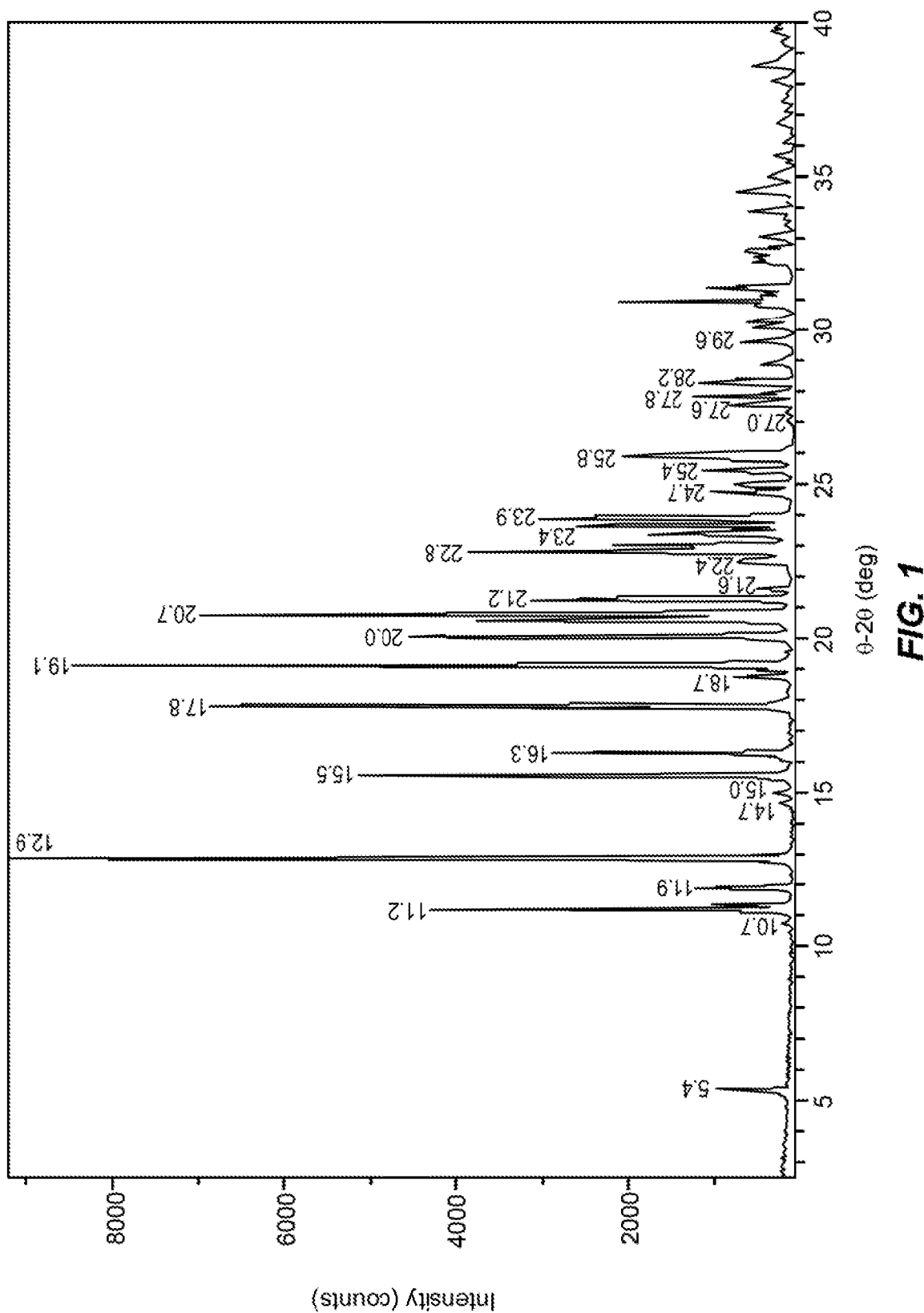
FIG. 1 provides the X-ray powder diffraction (XRPD) spectra of crystalline (2S,3R,4R,5S,6R)-2-(4-chloro-3-(4-(2-cyclopropoxyethoxy)benzyl)phenyl)-6-(hydroxymethyl) tetrahydro-2H-pyran-3,4,5-triol.

The present invention discloses a surprising species-dependence of the potency and selectivity of the compound bexagliflozin, originally developed for the treatment of human type 2 diabetes mellitus.

Bexagliflozin is a C-aryl glucoside that is a highly selective inhibitor of human Sodium-Glucose Linked Transporter 2 (SGLT2), an integral membrane protein expressed on the apical plasma membrane of tubular epithelium in the S1 and S2 segments of the kidney proximal tubule. It is responsible for the re-uptake of the majority of glucose in the filtrate under normal physiological conditions. Bexagliflozin has a selectivity for human SGLT2 of 2400-fold compared to human SGLT1. Bexagliflozin produces a prominent and saturable glucosuria in mice, rats, cats, dogs, rabbits, monkeys and humans. Experiments using rodent genetic models of diabetes have shown that even in the presence of a florid pre-existing glucosuria, bexagliflozin can produce a reduction in blood glucose levels and a partial alleviation of disease. Hence the existence of glucosuria does not preclude the application of bexagliflozin for the management of diabetes.

In the present invention bexagliflozin has been found to be 5 times more potent against feline SGLT2 than against human SGLT2, and 235 times more potent against feline SGLT1 than against human SGLT1. As a dual SGLT1/2 inhibitor in cats, bexagliflozin produces both desirable and undesirable effects characteristic of its mechanism of action. Notably, it elicits a prominent glucosuria and rapid palliation of hyperglycemia in diabetic cats, while also showing a tendency at high doses to induce the loose stools and diarrhea that are characteristic consequences of SGLT1 inhibition. Thus, the in vitro predictions of low selectivity are substantiated by in vivo observations.

In humans, null or hypomorphic mutations in the gene encoding SGLT1, SLC5A1, produce a severe neonatal diarrhea that is thought to reflect increased lumenal water abundance and microbial overgrowth. However, partial inhibition of SGLT1 will decrease the absorption of glucose (and, in at least some species, galactose) and so may reduce the effects of dietary carbohydrate on plasma glucose concentration, contributing to a therapeutically desirable outcome. Because the locus of action is the intestine, not the kidney, this benefit of a dual SGLT1 and 2 inhibitor should not decline with waning renal function, and hence may allow a diabetic cat with renal disease or impairment to benefit from the action of bexagliflozin. When an inhibitor has action on both SGLT1 and SGLT2 it can be described as an SGLT inhibitor.

To benefit from the action of a dual SGLT1 and 2 inhibitor, therefore, a balance must be struck. If the SGLT inhibitor has too high an activity on SGLT1 compared to SGLT2, the enteric effects will predominate, and the ensuing diarrhea, although not necessarily unfavorable for the hyperglycemia, will have an adverse effect on the owner and the owner's perception of the health of the cat. Adverse consequences of SGLT1 inhibition are not limited to diarrhea in humans and other species, and may include other enteric effects such as flatulence, abdominal distress and bloating.

Thus it is favorable to have an activity on SGLT1 that is lower than the activity on SGLT2. The optimal ratio cannot be estimated from the limited data available, but one factor to be kept in mind is the local concentration of the compound. When delivered by the oral route, the concentration of a drug in the lumen of the intestine can be many times higher than the concentration in plasma. Hence a relatively weak SGLT1 inhibitor may nonetheless have a relatively potent in vivo effect. Although in vitro data to some extent can help guide the selection of an appropriate mixed SGLT1 and 2 inhibitor, the best guide remains the assessment of actual effects in cats. The dose threshold for adverse enteric effects should be a few-fold higher than the smallest dose producing 90% of the maximum pharmacodynamic effect.

The frequency and severity of diarrhea may vary according to the diet of the cat or the weight, breed, medical history or other idiosyncratic factors. The threshold at which diarrhea or loose stools become objectionable to the owner is also subject to multiple influences. For the purpose of this description, an elevated frequency of diarrhea is any frequency that exceeds that of an unmedicated cat by more than ten percent of defecations. Accordingly, the preferred dual inhibitor produces an elevated frequency of diarrhea or loose stools in healthy cats at no less than three times, and more preferably five times, the smallest dose producing 90% of the maximum urinary glucose excretion in healthy cats fed a non-prescription general diet, such as a dry food diet.

Diarrhea provoked by SGLT1 inhibition can be reduced by provision of a diet low in carbohydrate. As mentioned above, cats are obligate carnivores and consume little carbohydrate in non-domesticated circumstances. In contrast, a commercial dry food diet for a non-diabetic cat may provide as much as 50% of the caloric value in the form of carbohydrates.

In some countries, prescription diets containing low carbohydrate content are available for the management of feline diabetes. These diets typically consist of wet (canned) food, although some dry food diets are also available that have reduced carbohydrate content. The ISFM panel recommendations state that although a preferred carbohydrate content has not been determined, diets with ≤12% of the caloric value derived from carbohydrate may be appropriate for diabetic cats (Sparkes et al., 2015; J Feline Med Surg 17:235). Several non-prescription canned food diets also have minimal carbohydrate content.

Much of the carbohydrate in dry food diets is contributed by grains or grain-derived sources, which typically comprise a negligible proportion of the natural diet. Diets with low grain content are offered by some cat food vendors as a healthier alternative to conventional diets. To the extent that these diets provide less of the metabolizable energy in the form of carbohydrates, they can be a useful addition to a diabetes management plan.

Bexagliflozin has been studied in diabetic mice, rats, and humans. With addition of the information below, the compound has now also been studied in cats. In each organism the compound has been found to reduce blood glucose levels and improve long-term measures of glycemic control, such as $HbA_{1c}$ in rodents or humans, or fructosamine in cats. In cats, however, the action of bexagliflozin is unusually potent and qualitatively superior to that observed in other organisms. In a high fraction of diabetic cats, bexagliflozin has produced a clinical remission of the disease, resulting in serum fructosamine concentrations that fall within the reference range for healthy cats. Despite the high potency of bexagliflozin in cats, signs of clinically significant hypoglycemia have not been observed to date. The combination of high potency and low risk make bexagliflozin a superior choice for the management of feline diabetes. Of particular interest and utility is the observation that bexagliflozin as a monotherapy has proven to restore fructosamine levels to within the testing laboratory normal reference range in a majority of cats in a field study in which the cats were administered their medications by owners in an unsupervised (home) context.

A surprising and important therapeutic benefit has been the gain in weight of treated cats, an effect that runs counter to the expected action of the compound in both healthy and diabetic animals. Weight loss has been a common and consistent observation among diabetic humans administered bexagliflozin, for example, and weight loss in cats administered an SGLT2 inhibitor is taught by US 2015/0164856.

As is apparent to those of skill in the art, the effectiveness of a medication is dependent on many factors, including the severity and duration of disease, the rate of metabolism of the active ingredient or its active metabolites, and the regularity with which the medication is administered. Errors in dosing, particularly omissions, can have a significant impact on the apparent utility of a medication. In actual practice, omissions are common and the degree to which omissions occur can be a determining factor in the effectiveness of a medication.

Comorbidities may also affect the effectiveness of a medication. For example, because dual SGLT1 and 2 inhibitors block renal reuptake of glucose, they can be expected to lose potency as renal filtration declines, either as a natural consequence of aging or because of advancing renal disease. Dual SGLT1 and 2 inhibitors of the present invention are not considered to be attractive management options for cats with severe renal disease, although they may be effective in the setting of mild to moderate renal compromise and have been found in clinical studies to be effective for cats spanning a range of ages.

When humans initially present with T2DM, they are rarely in the throes of a diabetic crisis. Instead, the disease gradually evolves and the diagnosis is made incidental to results from regular examinations, or because of patient complaints, such as thirst or frequent urination, that herald more advanced disease. However, cats with diabetes are often presented to the veterinarian in acute disease, with very high blood glucose levels, glucosuria, and weight loss. Characteristic hyperglycemia-associated clinical signs in cats include polydipsia (excessive water consumption), polyphagia (excessive food consumption), polyuria (excessive urination) and weight loss. Often it is the weight loss and malaise that trigger the owner's concern. Surprisingly, although cats with diabetes are undernourished because of the massive loss of glucose in their urine (by the renal mechanisms detailed above), administration of bexagliflozin, which increases urinary glucose secretion, paradoxically arrests the weight loss and allows many of the cats to gain weight. In a similar manner, administration of bexagliflozin to diabetic cats would be expected, by virtue of the mechanism of action, to worsen the hyperglycemia-associated clinical signs of polydipsia, polyphagia and polyuria, since these are all believed to arise mechanistically as a consequence of the disease-induced glucosuria. Against this expectation, though, administration of bexagliflozin to diabetic cats results in a reduction in the clinical signs of polydipsia, polyphagia and polyuria, even though the cats have been administered a medicament that would be expected to exacerbate these signs. They do, of course, continue to exhibit profound glucosuria because of the mechanism of action of the medication. Hence even though by its mechanism bexagliflozin would be expected to exacerbate hyperglycemia-associated clinical signs, in clinical studies it has reversed weight loss and allowed cats to return to normal or near-normal behavior.

A definitive explanation for the mechanism of improvement of hyperglycemia-associated clinical signs by bexagliflozin in diabetic cats has yet to be presented. However, it is possible that, by inhibiting SGLT1 and 2, enough additional glucose is discharged in the urine to result in a reduction in plasma glucose concentration. As the plasma glucose concentration drops, the proportion of glucosuria that is due to the effects of medication, as opposed to disease, increases, further improving the glycemic control. Eventually the rate of glucose excretion balances the excess glucose production and the hyperglycemia-associated clinical signs improve.

Diabetes in cats may be associated with acromegaly, a condition resulting from hyperplasia of the somatotrope compartment of the pituitary gland and resulting in inappropriate production of growth hormone. Elevated growth hormone in turn produces elevated insulin-like growth factor 1 (IGF-1), which antagonizes the action of insulin. Insulin resistance in diabetic cats is frequently associated with acromegaly (Scott-Moncrieff, J C, Vet Clin North Am Small Anim Pract (2010) 40:241), and it has been estimated that up to a quarter of diabetic cats in Europe may have underlying acromegaly (Niessen PLoS One. 2015 10:e0127794). Often very high doses of insulin are required to manage diabetic cats with acromegaly. An effective insulin-independent antidiabetic agent would be an important addition to the options for managing feline diabetes.

Described herein are methods and compositions for reducing the hyperglycemia of feline diabetes and hyperglycemia-associated clinical signs by administering Compound 1 (bexagliflozin). The methods described herein include specific dosing amounts and frequencies.

Surprisingly, administration of Compound 1 provides a therapeutic benefit to diabetic felines as a sole treatment agent that in a majority of animals, results in serum fructosamine levels that fall below the upper limit of normal of the testing laboratory reference range, that is, within the normal range for healthy cats. Compound 1 effectively treats diabetes in felines that are not receiving treatment with any other antidiabetic agent. Comparatively, when Compound 1 is administered to diabetic rats and mice, a restoration of the blood glucose levels or $HbA_{1c}$ to the normal range cannot be achieved. Similarly, when Compound 1 is administered to humans with T2DM, in many cases additional agents are required to restore blood glucose levels or $HbA_{1c}$ to the normal range.

Advantageously, Compound 1 does not produce hypoglycemia. Thus, administration of Compound 1 does not require the careful control of dosage or the timing of said dosage.

Further, in some instances, the methods of managing feline diabetes described herein result in clinical remission in said felines.

II. Definitions

"Compound 1" refers to the chemical (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, having the formula:

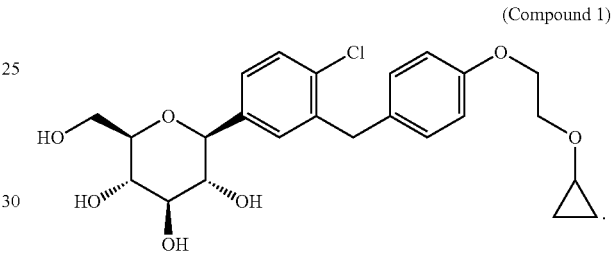

(Compound 1)

As used herein, "pharmaceutically acceptable form" refers to pharmaceutically acceptable salts, polymorphs, co-crystals, and monocrystalline forms of a given compound.

As used herein, "clinical remission" refers to a sustained reduction, abatement, or lessening in one or more clinical measures for a disease that cause the measures to fall within the accepted bounds for test values obtained from a healthy population. Such test values are said to fall "within the normal range." "Clinical remission" does not imply cessation of treatment. As used herein, "clinical remission" does not require that all clinical measures for a disease fall within the normal range. For example, a cat for which the serum fructosamine falls within the normal range, but for which the fasting serum glucose is greater than the upper limit of the normal range, is said to be in clinical remission.

As used herein, "normal ranges" can be dependent on the equipment and procedures of the testing laboratory and hence may vary from laboratory to laboratory. When values fall "within the normal range" as used herein, the phrase means within the range established by the particular laboratory providing the results at the time of measurement.

As used herein, "treatment-free remission" describes a state of remission that persists after cessation of administration of the therapeutic agent.

As used herein, "hyperglycemia-associated clinical signs" describes one or more of the characteristic signs of polydipsia, polyphagia, polyuria, or weight loss. Clinical signs of weight loss can be quantitated by direct measurement of the weight of a cat during an office visit. Recording of the other signs typically requires owner observation of cat behaviors or their consequences.

As used herein, the word "cat" when used as an adjective and the word "feline" are used interchangeably and mean of or pertaining to an animal from the family Felidae, including particularly a member of that family that is maintained as a pet or companion animal and that typically belongs to the genus *Felis*, species *silvestris catus* or species *catus* and is often referred to as a domestic cat or house cat.

As used herein, the word cat when used as a noun refers to a feline animal.

As used herein, "managing diabetes" or "management of diabetes" refers to the process by which an owner or other person responsible for the care of an animal addresses the disease by specific measures intended to palliate or cure the disease or provide relief of symptoms or change the perceived health of the animal by various means. Such means can include a change in the diet of the animal, including provision of a special or prescription diet or other change in the type or amount of food offered, or the encouragement or provision of activities that result in increased exertion or metabolic energy expenditure, or the provision of herbal preparations, dietary supplements or medicaments.

As used herein, "blood glucose", "blood glucose concentration" or "blood glucose levels" refer to measurements of glucose in whole blood. Typically, the sample drawn is capillary blood and the glucose is measured by a point-of-care device such as a glucometer.

As used herein, a "blood glucose curve" refers to the results of determining the glucose concentration in serial samples of whole blood obtained over a period of time typically ranging from 8 to 24 hours and undertaken as a means of assessing the degree of disease control and the appropriateness of the management, for example to determine if the amount of a therapeutic medicament is too great and an adversely low blood glucose is observed.

As used herein, "serum glucose", "serum glucose concentration" or "serum glucose level" refers to a glucose concentration that is measured in the liquid phase of whole, typically venous, blood that has been allowed to coagulate. Serum glucose concentrations are often determined in clinical practices by automated procedures performed in a diagnostic testing laboratory.

As used herein, "serum fructosamine", "serum fructosamine concentration" or "serum fructosamine level" refers to a fructosamine concentration that is measured in the liquid phase of whole, typically venous, blood that has been allowed to coagulate. Serum fructosamine concentrations are often determined in clinical practices by automated procedures performed in a diagnostic testing laboratory.

As used herein, "plasma glucose" or "plasma glucose concentration" refers to a glucose concentration that is obtained by measurement of the liquid phase of whole, typically venous, blood that has been separated from the cellular components of the blood in such a manner that the blood does not coagulate.

As used herein, the word "fasting" when applied to the circumstances surrounding the collection of a specimen for testing indicates that the animal from which the specimen was drawn had been deprived of food for an extended period of time, typically 6 hours or longer and not unusually overnight if the specimen is taken in the morning. A fasting sample is useful for the measurements of analytes such as glucose or lipids that are greatly affected by feeding.

As used herein, "reduction of hyperglycemia-associated clinical signs" as well as "an improvement of associated clinical signs" as it relates to hyperglycemia, means an improvement from the time of initiation of management of one or more of the signs of polydipsia, polyphagia, polyuria or the prevention of weight loss.

As used herein, an improvement in polydipsia means a decrease in the observed frequency or volume of water or fluids consumed, or a decrease in the frequency of seeking out unusual sources of water that the cat does not regularly consume.

As used herein, an improvement in polyphagia means a decrease in the amount of food consumed, or the frequency of begging or soliciting abnormal amounts of food, or the begging or soliciting of food under unusual circumstances, such as immediately following a feeding.

As used herein, an improvement in polyuria means a decrease in the frequency of urination or amount of urine produced, or a decrease in unusual behavior related to urination, including urination outside of a litter box provided for the purpose or flooding of the box.

As used herein, "prevention of weight loss" means resulting in a decrease in body weight no greater than 5% from the time of initiation of management. For avoidance of doubt "prevention of weight loss" encompasses any increase in body weight from the time of initiation of management.

As used herein, the definition of "hypoglycemia" refers to the clinical state in which the measured blood glucose concentration falls below the upper limit of the range for the ISFM definition (Sparkes et al., 2015; J Feline Med Surg 17:235) of a blood glucose<3.0-3.5 mM (53-63 mg dL$^{-1}$). For avoidance of doubt, hypoglycemia means a blood glucose<63 mg dL$^{-1}$.

Clinical markers for diabetes include, but are not limited to, serum fructosamine levels, blood or serum glucose levels, or glycated hemoglobin levels. A management regimen can be for at least 1, 3, 7, 14, 28, or more days; or 1, 2, 3, 4, or more months or for the remainder of the lifespan. In some embodiments, the management regimen is 2 months. In some embodiments the clinical remission is permanent, that is, persists for the lifespan of the cat. In some embodiments a management-free remission is achieved. In some embodiments the management-free remission duration is at least 1, 3, 7, 14, 28, or more days; or 1, 2, 3, 4, or more months or for the remainder of the lifespan. The amount of time the management-free remission lasts will depend on a number of factors including the feline, its diet, and amount of daily exercise. As a non-limiting example, clinical remission can be identified by a serum fructosamine level at or below the upper limit of normal for the testing laboratory reference range. As an additional non-limiting example, clinical remission can be identified by a fasting plasma glucose level of at or below 170 mg dL$^{-1}$.

As used herein "upper limit of normal" or "ULN" of a testing laboratory reference range means the least upper bound of the range of values for a laboratory test that are thought to be found within the normal variation of specimens drawn from a healthy population. The upper limit of normal is typically provided by the testing laboratory in connection with the transmission of test results to the practitioner and may vary from laboratory to laboratory or from time to time within a laboratory, depending on the test calibration, test conduct, or specimen preparation. For example, in the course of the field study reported below, a change in testing methodology at the central laboratory resulted in a shift in the upper limit of normal for serum fructosamine from 356 µmol L$^{-1}$ to 275 µmol L$^{-1}$.

As used herein "antidiabetic agent" refers to a composition comprising medicines, medications, or medicaments generally used in the treatment of diabetes in humans or the management of diabetes in animals. Common antidiabetic agents for the treatment of human T2DM include, but are not limited to alpha-glucosidase inhibitors, amylin analogs, biguanides, dipeptidyl peptidase 4 inhibitors, incretins or incretin mimetics, insulins, meglitinides, non-sulfonylurea secretagogues, SGLT2 inhibitors, sulfonylureas, and thiazolidinediones. It is generally accepted that oral medications for the treatment of T2DM in humans have little utility for the management of feline diabetes. To date no oral medication has been approved for the management of feline diabetes by a regulatory authority of the United States, the European Union, or Japan.

As used herein, "low carbohydrate diet" refers to the food intake of a feline from the time of initiation of management. In particular, a low carbohydrate diet is one where the relative amount of carbohydrates consumed does not exceed a certain threshold level. Low carbohydrate diets typically include less than 40%, 35%, 30%, 26%, 20%, 15%, 12% or lower percentage of calories from carbohydrate.

As used herein, "diabetic diet" refers to the food intake of a feline from the time of initiation of management. In particular, a diabetic diet is one that includes relatively high amounts of protein and low amounts of carbohydrates. High amounts of protein include 60%, 65%, 70%, 75%, 80% or greater percentage of calories from protein, while low amounts of carbohydrate are as defined above. In particular embodiments, a diabetic diet does not include dry cat food.

As used herein, an "elevated frequency of diarrhea or loose stools" means any frequency of diarrhea or loose stools that exceeds that of the unmedicated animal by more than ten percent of defecations. Diarrhea, as used herein, does not include incidental causes such as infection by a bacteria, virus, coccidian, or intestinal worms, but instead refers to diarrhea resulting from SGLT1 inhibition. In some embodiments, "diarrhea" refers to loose or liquid stools occurring at least once a day for at least three days during the course of treatment.

As used herein "SGLT inhibitor" refers to compounds that have activity against both SGLT1 and SGLT2, and especially those compounds that have a favorable proportion of SGLT2 activity to SGLT1 activity, such that the benefit of glucosuria and impaired absorption of enteric carbohydrate is accompanied by a low risk of unfavorable gastrointestinal symptoms such as diarrhea, loose stools, flatulence and bloating.

As used herein, the term "administering" means delivering by oral, buccal, nasal, rectal, vaginal or cutaneous routes or other topical contact, or by intravenous, intraperitoneal, intramuscular, intralesional or subcutaneous routes, or by the implantation of a slow-release device or preparation such as a pump, gel, reservoir or erodible substance to a subject. Administration can be by any route including parenteral, and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, intrathecal and intracranial. Other modes of delivery include, but are not limited to, the use of liposomal formulations, intravenous infusion, transdermal patches, and the like.

As used herein, a method of managing, inducing, reducing, improving, or preventing a disorder, disease, or condition comprising administering a compound or composition may also mean the use of a compound or composition for managing, inducing, reducing, improving, or preventing a disorder, disease, or condition, as well as the use of a compound or composition for preparation of a medicament for managing, inducing, reducing, improving, or preventing a disorder, disease, or condition.

III. Methods of Managing Feline Diabetes

In some aspects, provided herein are methods of managing feline diabetes, which methods include administering to a feline in need thereof a total daily dosage of about 5 to 50 mg of Compound 1, having the formula:

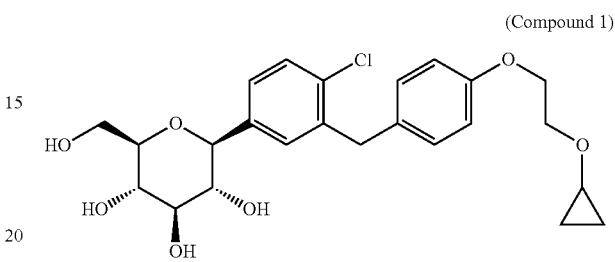

(Compound 1)

or a pharmaceutically acceptable form thereof.

In some aspects, provided herein are methods of reducing hyperglycemia-associated clinical signs in cats with diabetes mellitus, said method comprising administering to a feline in need thereof a total daily dosage of about 5 to 50 mg of Compound 1 or a pharmaceutically acceptable form thereof.

In some aspects, provided herein are methods of improving clinical signs associated with hyperglycemia in cats with diabetes mellitus, said method comprising administering to a feline in need thereof a total daily dosage of about 5 to 50 mg of Compound 1 or a pharmaceutically acceptable form thereof.

In some aspects, provided herein are methods of inducing clinical remission of diabetes in a cat, said method comprising administering to a feline in need thereof a total daily dosage of about 5 to 50 mg of Compound 1 or a pharmaceutically acceptable form thereof.

In some aspects, provided herein are methods of reducing the serum fructosamine level of a diabetic cat to below the upper limit of normal of the testing laboratory reference range, said method comprising administering to a cat in need thereof of a total daily dosage of about 5 to 50 mg of Compound 1 or a pharmaceutically acceptable form thereof. In some embodiments, the upper limit of normal for the testing laboratory reference is about 356 µmol $L^{-1}$ or about 275 mol $L^{-1}$.

In some aspects, provided herein are methods of improving the glycemic control of a diabetic cat such that the cat has a blood glucose curve in which all measurements of blood glucose fall in a range between a peak of 10 mmol/L (180 mg $dL^{-1}$) and a nadir of 4.5 mmol/L (80 mg $dL^{-1}$), said method comprising administering to a cat in need thereof of a total daily dosage of about 5 to 50 mg of Compound 1 or a pharmaceutically acceptable form thereof.

In some aspects, provided herein are methods of preventing the weight loss of a diabetic cat, said method comprising administering to a cat in need thereof of a total daily dosage of about 5 to 50 mg of Compound 1 or a pharmaceutically acceptable form thereof.

In some aspects, provided herein are methods for managing the diabetes of a cat exhibiting an IGF-1 concentration greater than the upper limit of normal for the testing laboratory reference range, comprising administering to a feline in need thereof a total daily dosage of about 5 to 50 mg of Compound 1 or a pharmaceutically acceptable form thereof.

In some embodiments, the upper limit of normal for the testing laboratory reference range is 92 nmol/L.

In some embodiments, the methods provided herein include administering to a feline in need thereof a low carbohydrate diet and a total daily dosage comprising about 5 to 50 mg of Compound 1. Carbohydrates are commonly present in commercial cat foods, and maintaining a low carbohydrate diet will improve the clinical pathology of the feline. In some embodiments, said low carbohydrate diet is a canned diet. Felines on a canned diet will not be fed any dry cat food. In some embodiments, said low carbohydrate diet is a diabetic diet. A diabetic diet is one that is generally high in protein and is low in carbohydrates. In some embodiments, a diabetic diet includes little or no dry cat food. In some embodiments, said low carbohydrate diet is a ketogenic diet. Ketogenic diets include diets that are high in seafood, meat, poultry, and eggs. In some embodiments, said low carbohydrate diet is a grain-free diet.

In some embodiments, said low carbohydrate diet contains less than 40% of calories in the form of carbohydrates. In some embodiments, said low carbohydrate diet contains less than 35% of calories in the form of carbohydrates. In some embodiments, said low carbohydrate diet contains less than 30% of calories in the form of carbohydrates. In some embodiments, said low carbohydrate diet contains less than 26% of calories in the form of carbohydrates.

In some embodiments, Compound 1 is a bis-proline complex of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, having the formula

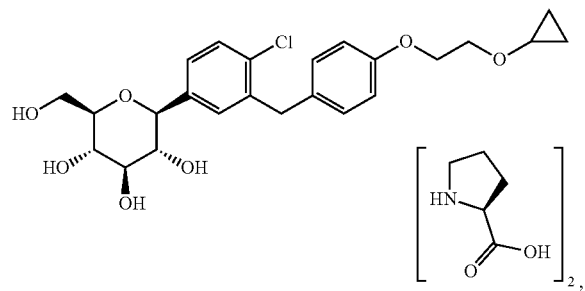

and said bis-proline complex of Claim 1 is administered to a feline in need thereof. Further information on the bis-proline complex is found in WO2010/022313, the contents of which is incorporated by reference herein for all purposes.

In some embodiments, Compound 1 is a crystalline form of (2S,3R,4R,5S,6R)-2-(4-chloro-3-(4-(2-cyclopropoxyethoxy)benzyl)phenyl)-6-(hydroxymethyl)tetrahydro-2H-pyran-3,4,5-triol, having the formula

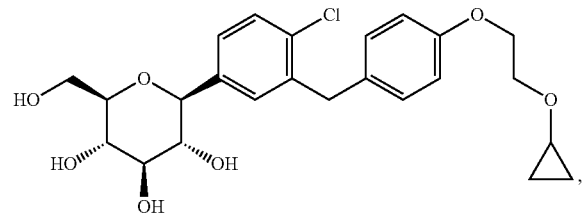 [SMILES: OC[C@H]1O[C@@H](c2ccc(Cl)c(Cc3ccc(OCCOC4CC4)cc3)c2)[C@H](O)[C@@H](O)[C@@H]1O]

and said crystalline form of Compound 1 is administered to a feline in need thereof.

The crystalline form of the compound is characterized by an X-ray powder diffraction pattern shown in FIG. 1. In some embodiments, the X-ray powder diffraction (XRPD) pattern includes one or more peaks at 5.4, 11.2, 11.3, 11.9, 12.9, 15.5, 16.3, 17.8, 19.1, 20.0, 20.6, 20.7, 21.2, 22.8, 23.0, 23.4, 23.6, 23.9, 24.7, 25.4, 25.8, 27.8 and 28.2 degrees 2θ (±0.1 degrees 2θ), wherein said XRPD is made using CuK$_{α1}$ radiation. In another embodiment, the crystalline form of the compound is characterized by an XRPD pattern that includes two or more, three or more, four or more, or five or more peaks at 5.4, 11.2, 11.3, 11.9, 12.9, 15.5, 16.3, 17.8, 19.1, 20.0, 20.6, 20.7, 21.2, 22.8, 23.0, 23.4, 23.6, 23.9, 24.7, 25.4, 25.8, 27.8 and 28.2 degrees 2θ (±0.1 degrees 2θ). In some other embodiments, the crystalline form of the compound is characterized by an XRPD pattern that includes peaks at 12.9, 19.1 and 20.7 degrees 2θ (±0.1 degrees 2θ). In still other embodiments, the crystalline form of the compound is characterized by an XRPD pattern that includes peaks at 11.2, 12.9, 15.5, 17.8, 19.1, 20.0 and 20.7 degrees 2θ (±0.1 degrees 2θ). In yet other embodiments, the crystalline form of the compound is characterized by an XRPD pattern that includes peaks at 5.4, 11.2, 11.9, 12.9, 15.5, 16.3, 17.8, and 19.1 degrees 2θ (±0.1 degrees 2θ). In still yet other embodiments, the crystalline form of the compound is characterized by an XRPD pattern that includes peaks at 5.4, 11.2, 11.9, and 12.9 degrees 2θ (±0.1 degrees 2θ). In another embodiment, the crystalline form of the compound is characterized by an XRPD pattern including peaks at 11.2 and 12.9 degrees 2θ (±0.1 degrees 2θ). In other embodiments, the crystalline form of the compound is characterized by the XRPD peaks substantially in accordance with FIG. 2.

Figure 3:
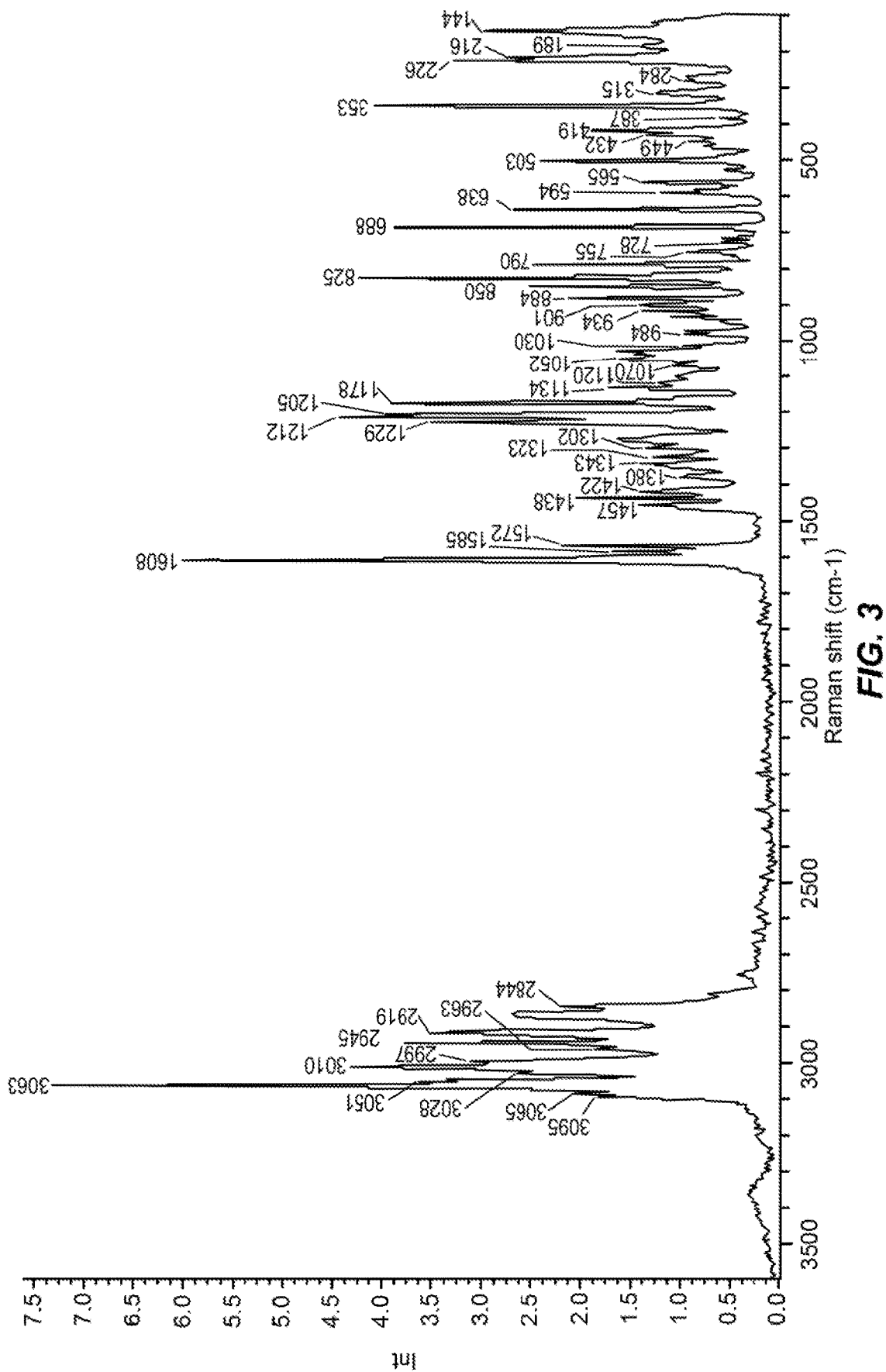
FIG. 3 provides the Raman spectra of crystalline (2S,3R, 4R,5S,6R)-2-(4-chloro-3-(4-(2-cyclopropoxyethoxy)benzyl)phenyl)-6-(hydroxymethyl)tetrahydro-2H-pyran-3,4,5-triol.

The crystalline compound of the present invention is also characterized by the Raman spectra substantially in accordance with FIG. 3 and the peaks substantially in accordance with FIG. 4. In some embodiments, the crystalline form of the compound is characterized by a Raman spectra that includes one or more peaks at about 353, 688, 825, 1178, 1205, 1212, 1608, 2945, 3010 and 3063 cm$^{-1}$. In another embodiment, the crystalline form of the compound is characterized by a Raman spectra that includes two or more, three or more, four or more, or five or more peaks. In other embodiments, the crystalline form of the compound is characterized by the Raman spectra including peaks at about 353, 688 and 825 cm$^{-1}$. In some other embodiments, the crystalline form of the compound is characterized by the Raman peaks substantially in accordance with FIG. 4.

In some embodiments, the therapeutically effective amount of Compound 1 is a total daily dosage of about 5 mg to 50 mg (e.g., about 5, 7.5, 10, 12.5, 15, 17.5, 20, 22.5, 25, 30, 35, 40, 45 or 50 mg day$^{-1}$). In some embodiments, the total daily dosage of Compound 1 is about 10 to 20 mg. In some embodiments, the total daily dosage of Compound 1 is about 15 mg, Compound 1 may be administered to felines via a number of suitable routes. In some embodiments, Compound 1 is administered orally. Further methods of administration are discussed in the sections below.

In some embodiments, Compound 1 is administered in combination with an additional therapeutic agent. In some embodiments, Compound 1 is administered as a monotherapy. That is, a positive therapeutic benefit in managing feline diabetes is imparted when Compound 1 is the only antidiabetic agent administered to a feline.

Advantageously, administration of Compound 1 does not need to be timed with a meal or other event. In some embodiments, the total daily dosage is administered once daily independent of other activities (including meal timing). In some embodiments, the total daily dosage is administered twice daily independent of other activities (including meal timing). In some embodiments, the dosage is admixed with the cat's food. In some embodiments the dosage is delivered to the cat as a single solid dosage form. In some embodiments the dosage is delivered as an oral solution or oral suspension. In some embodiments the maximum fluid volume delivered is 1 mL. In some embodiments the maximum volume delivered is 0.5 mL. In some embodiments the dosage is adjusted according to the weight of the cat. In some embodiments a single dosage strength is provided for all cats.

Over the course of management, the serum fructosamine levels and/or blood or serum glucose levels can be monitored for evidence of glycemic control. Clinical signs such as polyuria, polydipsia, polyphagia or weight loss may also be monitored. If continuing signs of diabetes persist, the management plan may be changed to include other features, including other medications.

When a feline is maintaining clinical remission, the feline sustains the positive therapeutic benefit received from the therapeutic regimen received. In some embodiments, clinical remission is maintained when the feline does not present one or more clinical markers for feline diabetes. As discussed above, the symptoms of feline diabetes include elevated levels of serum fructosamine, elevated levels of blood or serum glucose levels, polyuria, polydipsia, and polyphagia.

In some embodiments, a feline maintaining clinical remission is determined by the feline's serum fructosamine levels. In some embodiments, the feline's serum fructosamine level is compared to the upper limit of normal for the testing laboratory reference range. In some embodiments, the upper limit of normal for the testing laboratory reference is about 356 µmol $L^{-1}$ or about 275 µmol $L^{-1}$. In some embodiments, the feline in clinical remission exhibits a serum fructosamine level at or below the upper limit of normal for the testing laboratory reference range. In some embodiments, the feline in clinical remission exhibits a serum fructosamine level at or below 360 µmol $L^{-1}$. In some embodiments, the feline in clinical remission exhibits a serum fructosamine level at or below 350 µmol $L^{-1}$. In some embodiments the feline in clinical remission exhibits a serum fructosamine level that is at or below the upper limit of normal for the testing laboratory to which the specimen has been submitted.

In some embodiments, a feline maintaining clinical remission is determined by the feline's blood or serum glucose levels. In some embodiments, the feline in clinical remission maintains a blood or serum glucose level of less than 250 mg $dL^{-1}$. In some embodiments, the feline in clinical remission maintains a blood or serum glucose level of less than 200 mg $dL^{-1}$. In some embodiments, the feline in clinical remission maintains a blood or serum glucose level of less than 190 mg $dL^{-1}$. In some embodiments, the feline in clinical remission maintains a blood or serum glucose level of less than 180 mg $dL^{-1}$. In some embodiments, the feline in clinical remission maintains a blood or serum glucose level of less than 170 mg $dL^{-1}$. In some embodiments, the feline in clinical remission maintains a blood or serum glucose level of less than 160 mg $dL^{-1}$. In some embodiments, the feline in clinical remission maintains a blood or serum glucose level of less than 150 mg $dL^{-1}$.

The methods described herein reduce, lessen, or eliminate symptoms of feline diabetes. For example, in some embodiments, a feline's serum fructosamine level, as measured after completion of a management regimen, is reduced in said feline. In some embodiments, a feline's blood or serum glucose level, as measured after completion of a management regimen, is reduced in said feline.

In some embodiments, the feline's serum fructosamine level is reduced by at least about 20% after completion of said management regimen. In some embodiments, the feline's serum fructosamine level is reduced by at least about 30% after completion of said management regimen. In some embodiments, the feline's serum fructosamine level is reduced by at least about 40% after completion of said management regimen. In some embodiments, the feline's serum fructosamine level is reduced by at least about 50% after completion of said management regimen.

In some embodiments, the feline's serum fructosamine level is less than the upper limit of normal for the testing laboratory reference range after completion of said management regimen. In some embodiments, the upper limit of normal for the testing laboratory reference is about 356 µmol $L^{-1}$ or about 275 µmol $L^{-1}$. In some embodiments, the feline's serum fructosamine level is less than 500 µmol $L^{-1}$ after completion of said management regimen. In some embodiments, the feline's serum fructosamine level is less than 450 µmol $L^{-1}$ after completion of said management regimen. In some embodiments, the feline's serum fructosamine level is less than 400 µmol $L^{-1}$ after completion of said management regimen. In some embodiments, the feline's serum fructosamine level is less than 350 µmol $L^{-1}$ after completion of said management regimen.

In some embodiments, the feline's blood or serum glucose level is reduced by at least about 20% after completion of said management regimen. In some embodiments, the feline's blood or serum glucose level is reduced by at least about 30% after completion of said management regimen. In some embodiments, the feline's blood or serum glucose level is reduced by at least about 40% after completion of said management regimen. In some embodiments, the feline's blood or serum glucose level is reduced by at least about 50% after completion of said management regimen.

In some embodiments, the feline's blood or serum glucose level is less than 250 mg $dL^{-1}$ after completion of said management regimen. In some embodiments, the feline's blood or serum glucose level is less than 200 mg $dL^{-1}$ after completion of said management regimen. In some embodiments, the feline's blood or serum glucose level is less than 190 mg $dL^{-1}$ after completion of said management regimen. In some embodiments, the feline's blood or serum glucose level is less than 180 mg $dL^{-1}$ after completion of said management regimen. In some embodiments, the feline's blood or serum glucose level is less than 170 mg $dL^{-1}$ after completion of said management regimen. In some embodiments, the feline's blood or serum glucose level is less than 160 mg $dL^{-1}$ after completion of said management regimen. In some embodiments, the feline's blood or serum glucose level is less than 150 mg $dL^{-1}$ after completion of said management regimen.

As discussed supra, it is favorable to have an activity on SGLT1 that is lower than the activity of SGLT2, and that SGLT1 inhibition can provoke diarrhea. Thus, SGLT inhibitors of the present disclosure provide a pharmacodynamic effect in the treatment of feline diabetes at a dosage level beneath the threshold level of adverse enteric effects. As such, in an additional aspect, provided herein are methods of managing feline diabetes, which includes administering to a feline in need thereof an effective amount of a SGLT inhibitor, wherein said effective amount is no more than 10 to 30% of the dose required to produce an elevated frequency of diarrhea or loose stool in a healthy feline. In some embodiments, the healthy feline is on a commercial dry food diet. In some embodiments, the healthy feline is one which is not exhibiting elevated frequency of diarrhea or loose stool prior to administration of a SGLT inhibitor. In some embodiments, the healthy feline is non-diabetic.

In some embodiments, the effective amount is no more than 10, 12, 16, 18, 20, 22, 24, 26, 28, or 30% of the dose required to produce an elevated diarrhea or loose stool in a healthy feline. In some embodiments, the effective amount is no more than 30% of the dose required to produce an elevated diarrhea or loose stool in a healthy feline. In some embodiments, the effective amount is no more than 20% of the dose required to produce an elevated diarrhea or loose stool in a healthy feline. In some embodiments, the effective amount is no more than 10% of the dose required to produce an elevated diarrhea or loose stool in a healthy feline.

An effective amount includes a dose that produces at least 90% percent of the maximum pharmacodynamics effect of said SGLT inhibitor.

Also provided herein are methods of managing feline diabetes, which includes administering to a feline in need thereof an effective amount of a SGLT inhibitor, wherein said SGLT inhibitor produces an elevated frequency of diarrhea or loose stools in a healthy feline at a dose of no less than 3 to 10 times said effective amount. In some embodiments, the healthy feline is on a commercial dry food diet. In some embodiments, the healthy feline is one which is not exhibiting elevated frequency of diarrhea or loose stool prior to treatment. In some embodiments, the healthy feline is non-diabetic.

In some embodiments, the SGLT inhibitor produces an elevated frequency of diarrhea or loose stools in a healthy feline at a dose of no less than 3, 4, 5, 6, 7, 8, 9, or 10 times the effective amount. In some embodiments, the SGLT inhibitor produces an elevated frequency of diarrhea or loose stools in a healthy feline at a dose of no less than 3 times the effective amount. In some embodiments, the SGLT inhibitor produces an elevated frequency of diarrhea or loose stools in a healthy feline at a dose of no less than 5 times the effective amount. In some embodiments, the SGLT inhibitor produces an elevated frequency of diarrhea or loose stools in a healthy feline at a dose of no less than 10 times the effective amount.

An effective amount includes a dose that produces at least 90% percent of the maximum pharmacodynamics effect of said SGLT inhibitor.

The methods described herein are useful in managing all forms of feline diabetes. In some embodiments, the feline diabetes is type 1 diabetes. In some embodiments, the feline diabetes is type 2 diabetes.

IV. Pharmaceutical Compositions

Compound 1 can be prepared in various compositions suitable for delivery to a subject. A composition suitable for administration to a subject typically comprises Compound 1, (or a pharmaceutically acceptable form thereof and a pharmaceutically acceptable carrier.

Compound 1 can be incorporated into a variety of formulations for therapeutic administration. More particularly, Compound 1 can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, Compound 1 can be administered in a local rather than systemic manner, for example, in a depot or sustained release formulation.

The pharmaceutical compositions for the administration of Compound 1 can conveniently be presented in unit dosage form and can be prepared by any of the methods known in the art of pharmacy and drug delivery. All methods include the step of bringing the active ingredient into association with a carrier containing one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation.

Suitable formulations for use in the present invention are found in Remington: THE SCIENCE AND PRACTICE OF PHARMACY, 21st Ed., Gennaro, Ed., Lippincott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In some embodiments, Compound 1 is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering Compound 1 (in any of the forms described herein) include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440;

6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, Compound 1 can be readily formulated by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient in need thereof. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Tablets of the current disclosure contain the active ingredient in admixture with non-toxic pharmaceutically acceptable excipients which are suitable for the manufacture of tablets. These excipients may be, for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Formulations for oral use may also be presented as hard gelatin capsules wherein the active ingredient is mixed with an inert solid diluent, for example, microcrystalline cellulose, lactose, starch, pregelatinized starch or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

In some instances, Compound 1 can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, Compound 1 can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain agents such as suspending, stabilizing and/or dispersing agents.

Pharmaceutical formulations for parenteral administration include aqueous solutions of Compound 1 (in any of the forms noted herein) in water-soluble form. Additionally, suspensions of Compound 1 can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, Compound 1 can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, Compound 1 can be formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

In addition to the formulations described previously, Compound 1 can also be formulated as a depot preparation. Such long acting formulations can be administered by implantation (for example subcutaneously or intramuscularly) or by intramuscular injection. Thus, for example, Compound 1 can be formulated with suitable polymeric or hydrophobic materials (for example as an emulsion in an acceptable oil) or ion exchange resins, or as sparingly soluble derivatives, for example, as a sparingly soluble complex or salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

V. Pharmaceutical Dosage Forms

The present disclosure includes novel pharmaceutical dosage forms of Compound 1, or a pharmaceutically acceptable form thereof. The dosage forms described herein are suitable for oral administration to a subject. The dosage form may be in any form suitable for oral administration, including, but not limited to, a capsule or a tablet.

In some embodiments, the present disclosure provides a single unit dosage capsule or tablet form containing 5 to 50 mg of Compound 1, (bexagliflozin), having the formula:

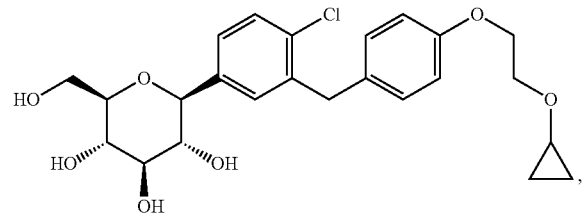 [SMILES: OC[C@H]1O[C@@H](c2ccc(Cl)c(Cc3ccc(OCCOC4CC4)cc3)c2)[C@H](O)[C@@H](O)[C@@H]1O]

or a crystalline form thereof.

In some embodiments, the amount of Compound 1 is from about 10 to 20 mg. In some embodiments, the amount of Compound 1 is about 15 mg.

In some embodiments, the single unit dosage form of Compound 1 is a capsule. In some embodiments, the single unit dosage form of Compound 1 is a tablet.

In some embodiments, the single unit dosage form is in a capsule of size #0, #1, #2, #3, #4, or #5. In some embodiments, the single unit dosage form is in a capsule of size #4. In some embodiments, the single unit dosage form is in a capsule of size #5.

VI. Kits

Also provided herein are kits comprising pharmaceutical compositions and dosage forms of Compound 1, or forms thereof.

In some aspects, the present invention provides a kit that includes Compound 1. Some of the kits described herein include a label describing a method of administering Compound 1. Some of the kits described herein include a label describing a method of managing feline diabetes. In some embodiments, the kits described herein include a label describing a method of reducing a feline's serum fructosamine and/or blood or serum glucose levels.

The compositions of the present invention, including but not limited to, compositions comprising Compound 1 in a bottle, jar, vial, ampoule, tube, or other container-closure system approved by the United States Food and Drug Administration (FDA) or other regulatory body, which may provide one or more dosages containing the compounds. The package or dispenser may also be accompanied by a notice associated with the container in a form prescribed by a governmental agency regulating the manufacture, use, or sale of pharmaceuticals, the notice indicating approval by the agency. In certain aspects, the kit may include a formulation or composition as described herein, a container closure system including the formulation or a dosage unit form including the formulation, and a notice or instructions describing a method of use as described herein.

EXAMPLES

The following examples are offered for illustrative purposes, and are not intended to limit the invention in any manner. Those of skill in the art will readily recognize a variety of noncritical parameters which can be changed or modified to yield essentially the same results.

Example 1. Effects of bexagliflozin in Diabetic Mice

In study 350, the effects of bexagliflozin (as the 2:1 proline:bexagliflozin cocrystal) were examined in genetically diabetic db/db mice. Blood glucose was measured using a glucometer (One Touch Ultra Johnson & Johnson (LifeScan) Blood Glucose Monitoring System). Generally, the blood was obtained from a cut in the tail. When the blood glucose values were higher than 33.3 mmol/L, the upper limit of quantification of the glucometer, two drops of blood were obtained from the orbital plexus and collected in anti-coagulated microcentrifuge tubes containing heparin for subsequent dilution and measurement of blood glucose. The masses of bexagliflozin in Table 1 are approximately ⅔ of the masses of 2:1 composition.

The animals were dosed daily with the vehicle or proline:bexagliflozin cocrystal by gavage administration for 28 days. Animals were dosed between 10:00 AM and 12:00 PM daily. The body weights were measured every 4 days and the dosage was adjusted according to the latest body weight. The volume of administration was 10 mL kg$^{-1}$ body weight. All animals were observed daily and any abnormal findings were recorded. Blood glucose concentrations were determined on days −3, 0, 1, 7, 14, 21 and 28 at 6 h post-dose.

As shown in Table 1, except for the 0.1 mg kg$^{-1}$ group, the non-fasting blood glucose of all treatment groups was significantly lower on days 1, 7, 14, 21, and 28 compared with the control group. Bexagliflozin lowered non-fasting blood glucose level of db/db mice in a dose-dependent manner at 6 h post-dose. The blood glucose values of animals following a 28-day administration of 0.067, 0.2, 0.67, and 2 mg kg$^{-1}$ bexagliflozin were 79.74%, 56.33%, 51.81%, and 53.25% of control, respectively. Although these data show that bexagliflozin is an effective anti-diabetic agent in diabetic mice, none of the dose groups exhibited normalization of the blood glucose concentration to within the non-diabetic range. For fasting mice of the C57/BL6 strain (the non-diabetic reference strain for db/db mice), the average fasting glucose has been reported to be 7.3 mM (131 mg dL$^{-1}$; Andrikopoulos et al., 2005; J Endocrinol (2005) 187:45). Typically, blood glucose levels greater than 180 mg dL$^{-1}$ are considered to be a sign of diabetes. However, bexagliflozin as a sole agent in db/db mice did not reduce blood glucose below 300 mg dL$^{-1}$.

TABLE 1

Effects of treatment with bexagliflozin on non-fasting blood glucose concentration (mg dL$^{-1}$) in db/db mice

| Group | Day −3 | Day 0 | Day 1 | Day 7 | Day 14 | Day 21 | Day 28 |
|---|---|---|---|---|---|---|---|
| Control | 559.7 ± 83.0 | 566.3 ± 110.2 | 535.7 ± 56.1 | 569.2 ± 65.4 | 550.6 ± 50.6 | 580.1 ± 29.5 | 592.0 ± 107.4 |
| 0.067 mg kg$^{-1}$ | 563.6 ± 105.2 | 565.5 ± 75.9 | 526.0 ± 97.0 | 459.5 ± 69.9* | 441.7 ± 119.6 | 497.5 ± 98.8 | 472.1 ± 113.3* |
| 0.2 mg kg$^{-1}$ | 546.9 ± 92.8 | 590.0 ± 92.9 | 411.3 ± 86.8** | 390.8 ± 92.3** | 364.7 ± 121.6* | 379.8 ± 47.4** | 333.5 ± 79.9** |

TABLE 1-continued

Effects of treatment with bexagliflozin on non-fasting blood glucose concentration (mg dL$^{-1}$) in db/db mice

| Group | Day −3 | Day 0 | Day 1 | Day 7 | Day 14 | Day 21 | Day 28 |
|---|---|---|---|---|---|---|---|
| 0.67 mg kg$^{-1}$ | 565.5 ± 87.5 | 574.4 ± 90.5 | 404.3 ± 86.4** | 370.1 ± 96.5** | 379.6 ± 58.6** | 300.6 ± 97.6** | 306.7 ± 98.4** |
| 2 mg kg$^{-1}$ | 603.9 ± 88.9 | 541.6 ± 84.4 | 382.7 ± 111.9** | 330.8 ± 101.1** | 303.5 ± 74.0** | 319.7 ± 74.2** | 315.2 ± 81.3** |

*P < 0.05.
**p < 0.01 vs. control
Compound or vehicle was orally administered once a day for 4 weeks. Blood glucose was determined at 6 hours post-dose without fasting using a glucometer. Values represent the mean ± SD. (n = 8). Groups were administered bexagliflozin/proline cocrystal at doses 1.5 times greater than the masses for bexagliflozin (shown).

Example 2. Effects of bexagliflozin in Diabetic Rats

In study 338, the effects of bexagliflozin (as the 2:1 proline:bexagliflozin cocrystal) were examined in genetically diabetic ZDF rats. Blood was collected from the saphenous vein of male ZDF rats in Capiject tubes containing sodium fluoride and potassium oxalate (Lot #HA0931; Terumo Medical Corp.) and used to determine non-fasted plasma glucose levels. Plasma glucose levels were analyzed by a colorimetric assay based on hexokinase methodology (Glucose-SL assay: Diagnostic Chemicals Ltd.). Plasma samples required 1:2 dilutions with 0.9% saline according to the manufacturer's instructions prior to analyses.

Animals were orally dosed by gavage once daily (9:00-11:00 am) with vehicle (10% PEG400) or experimental compound at one of four dose levels (0.067, 0.2, 0.67 and 2.0 mg kg$^{-1}$) for 28 days. Body weights were measured 3 times per week, and dosage was adjusted accordingly. Food (Purina 5008; Formulab Diet) and water consumption were measured 3 times per week and daily values estimated. 24 h food and water consumption were recorded during urine collection in metabolic cages. All animals were observed daily and any abnormal findings were recorded.

On Days 7, 14, and 21, blood samples were collected from the saphenous vein (Capiject Lot #HA0931; Terumo Medical Corp.) for determination of plasma glucose levels, followed by oral administration of compound or vehicle.

Daily oral treatment with bexagliflozin resulted in significant reductions in plasma glucose levels in as few as 7 days. No significant difference in plasma glucose was found among any of the groups at the initiation of dosing, as study groups were constituted to minimize inter-group variation in this variable (F(4,45)=0.04; p=0.99). On Day 7 of treatment, significantly reduced plasma glucose levels were observed (F(4,45)=3.99; p=0.007); pairwise comparisons revealed that plasma glucose levels were lower in all the groups receiving bexagliflozin except the lowest dose (p<0.05 for 0.2 and 0.67 mg kg$^{-1}$ and p<0.01 for 2.0 mg kg$^{-1}$) compared to the vehicle control (Table 2). Reductions from baseline were also significant (F(4,45)=4.05; p=0.007), with follow-up comparisons again revealing reductions in all but the 0.067 mg kg$^{-1}$ bexagliflozin treatment group to be significantly greater (p<0.05 for 0.3 and 1.0 mg kg$^{-1}$ and p<0.01 for 3.0 mg kg$^{-1}$) than the gain in plasma glucose level observed in the vehicle control (Table 2). The change in plasma glucose levels observed after 7 days were as follows: +2.8%, −16.8%, −17.1%, and −25.3%, for bexagliflozin at 0.067, 0.2, 0.67, and 2.0 mg kg$^{-1}$, respectively and +9.6% for vehicle control.

Following 2 weeks of treatment, reduced plasma glucose levels were observed (F(4,45)=12.3; p<0.0001); pairwise comparisons revealed that plasma glucose levels were significantly lower in all but the 0.067 mg kg$^{-1}$ bexagliflozin group compared to the vehicle control: p<0.01, for bexagliflozin at 0.2, 0.67 and 2.0 mg kg$^{-1}$ (FIG. 1 and Table 1). Likewise, reductions from baseline following 2 week treatment were also significant (F(4,45)=5.13; p=0.002), with the reductions produced by bexagliflozin at 2.0 mg kg$^{-1}$ being significantly greater than the vehicle control (p<0.01) (Table 2). The change in plasma glucose levels observed after 14 days were +9.5%, −5.6%, −8.1% and −25.1% for bexagliflozin at 0.067, 0.2, 0.67, 2.0 mg kg$^{-1}$, respectively and +17.0% for the vehicle control.

Similarly, after 3 weeks of treatment plasma glucose levels were significantly reduced (F(4,44)=7.77; p<0.0001); plasma glucose levels were significantly lower in the EGT0001474 groups receiving 0.3, 1.0 and 3.0 mg kg$^{-1}$ (p<0.05, <0.01 and <0.01, respectively) (Table 2).

Reductions from baseline were again significant (F(4,44)=3.36; p=0.017), with the reduction produced by bexagliflozin at 2.0 mg kg$^{-1}$ being significantly greater than the vehicle control (p<0.01) (Table 2). The change in plasma glucose levels observed after 21 days were as follows: +15.5%, +4.3%, +1.5% and −15.4%, for bexagliflozin at 0.067, 0.2, 0.67, 2.0 mg kg$^{-1}$, respectively and +25.5% for vehicle control. One rat receiving bexagliflozin at 0.67 mg kg$^{-1}$ was euthanized due to moribund condition prior to the Day 21 blood draw. Necropsy results suggested that this animal may have aspirated some dosing solution during the prior weeks of dosing. This effect was not considered to be test article-related. Data for the euthanized animal were retained in the Day 7 and Day 14 analyses, but not the Day 21 analyses (hence the reduced degrees of freedom in the denominator of the F statistic).

Although these data show that bexagliflozin is an effective anti-diabetic agent in diabetic rats, none of the dose groups exhibited normalization of the blood glucose concentration to within the non-diabetic range. Typically, blood glucose levels greater than 180 mg dL$^{-1}$ are considered to be a sign of diabetes. However, bexagliflozin as a sole agent in ZDF rats did not reduce blood glucose below 287 mg dL$^{-1}$ (Table 2).

TABLE 2

Chronic effects of bexagliflozin oral dosing on plasma glucose levels of male Zucker Diabetic Fatty rats.

| Group[a] | Day 0 | Day 7 | Day 14 | Day 21 | Day 21 Δ |
|---|---|---|---|---|---|
| Control | 385.2 ± 24.7 | 422.4 ± 22.9 | 450.7 ± 17.7 | 482.5 ± 10.6 | +97.3 ± 26.3 |
| 0.067 mg kg$^{-1}$ | 373.2 ± 29.5 | 383.7 ± 33.1 | 408.6 ± 19.6 | 431.0 ± 19.7 | +57.8 ± 41.7 |
| 0.2 mg kg$^{-1}$ | 386.6 ± 28.2 | 321.8 ± 19.5* | 364.9 ± 13.1** | 403.2 ± 20.1* | +16.6 ± 36.6 |
| 0.67 mg kg$^{-1}$ | 384.4 ± 27.5 | 318.7 ± 32.0* | 353.4 ± 18.9** | 374.2 ± 37.3** | +5.4 ± 30.8[b] |
| 2 mg kg$^{-1}$ | 384.8 ± 16.5 | 287.4 ± 27.4** | 288.3 ± 17.1** | 325.4 ± 13.0** | −59.4 ± 22.4** |

[a]Groups were administered bexagliflozin/proline at doses 1.5 times greater than the masses for bexagliflozin (shown).
[b]Euthanized prior to Day 21 blood sampling; n = 10 for Day 0 but n = 9 for Day 21 and Day 21 Delta (therefore, subtraction of means results in a different value than what is represented in the table: −10.2 g).

As the foregoing studies indicate, administration of bexagliflozin to diabetic rodents substantially ameliorates the severity of their disease, but does not restore the animals to the euglycemic state or produce plasma glucose levels within the normal range.

Example 3. Effects of bexagliflozin on Feline SGLT1 and 2 Transporters In Vitro In study 5, a DNA fragment encoding feline SGLT2 was inserted downstream of a cytomegalovirus immediate early protein enhancer/chicken β-actin promoter with a rabbit β-globin intron (CAG promoter) between the SalI and Hind III sites of mammalian expression vector pNL715 (pPB-CAG-SGLT2Cat-IRES-EGFP; Egret Pharma Shanghai, 1118 Halei Road 4F, Zhangjiang Hi-Tech Park, Shanghai China 201203). The plasmid expression cassette was flanked by PiggyBac transposon inverted terminal repeats and contained an internal ribosome entry site (IRES) upstream of an enhanced GFP open reading frame and a bovine growth hormone polyadenylation signal. Plasmids harboring the desired cDNA inserts were identified by restriction enzyme cleavage analysis. A plasmid (pNL717) encoding feline SGLT1 was similarly inserted between SalI and Hind III sites to create pPB-CAG-SGLT1Cat-IRES-EGFP (Egret Pharma Shanghai). A C-to-T transition mutation at position 891 in the fSGLT1 coding region of the cDNA clone (creating a stop codon at amino acid residue 297) was reverted to the wild-type sequence by polymerase chain reaction. Reversion restored activity to the expression plasmid.

Feline SGLT expression plasmid DNAs were transfected into Cos-7 cells using Lipofectamine 3000 (Thermo Fisher Corporation, Waltham, MA) according to the manufacturer's suggested protocol. Cells were seeded 24 hours prior to transfection in a 100 mm dish at approximately 3×10$^6$ cells/well in 10 mL of medium and were over 95% confluent at the time of transfection. The transfected cells were harvested 24 hours post-transfection using trypsin and seeded into DMEM supplemented with 10% FBS, 2 mM glutamine, 100 μL per well in 96-well poly D-lysine coated ScintiPlates (Perkin Elmer) that were then incubated in an atmosphere of 5% CO$_2$ at 37° C. for 48 h. Transfected cells were cryopreserved in DMEM containing 10% DMSO at −195° C. or were evaluated for transporter activity by a methyl-α-D-[U-$^{14}$C]glucopyranoside (AMG) uptake assay. Transfected cells expressing SGLT1 or SGLT2 (4×10$^4$ cells per well) were washed with 150 μL of either sodium buffer (137 mM NaCl, 5.4 mM KCl, 2.8 mM CaCl$_2$, 1.2 mM MgCl$_2$, 10 mM Tris/HEPES, pH 7.2) or sodium-free buffer (137 mM N-methylglucamine, 5.4 mM KCl, 2.8 mM CaCl$_2$, 1.2 mM MgCl$_2$, 10 mM Tris/HEPES, pH 7.2) twice. Either 50 μL of the sodium free buffer containing 40 μCi/mL α-methyl-D-glucopyranoside (AMG; Perkin Elmer) or 50 μL of the sodium buffer containing 8 μCi/mL AMG, 10% cat plasma and bexagliflozin at the desired concentrations were added to each well of the plate and incubated at 37° C. with shaking for 1 h. Cells were washed twice with 150 μL of phosphate buffered saline and the plates covered with TopSeal (Perkin Elmer) and AMG uptake was quantitated using a model 1450 MicroBeta Trilux microplate scintillation counter (PerkinElmer Corporation). Results of AMG uptake were analyzed using GraphPad Prism (Intuitive Software for Science). IC$_{50}$ calculations were performed using nonlinear regression with variable slope.

Bexagliflozin exhibited high potency against cat SGLT1 and SGLT2 with IC$_{50}$ values of 23.8 nM and 412 pM, respectively in the presence of 10% cat plasma. Compared to its activity against the cognate human transporters (Zhang et al., Pharmacological Research 63:284 2011), bexagliflozin is 5 times more active against feline SGLT2 and 235 times more active against feline SGLT1.

Example 4. Effects of bexagliflozin in Nondiabetic Cats

Figure 5:
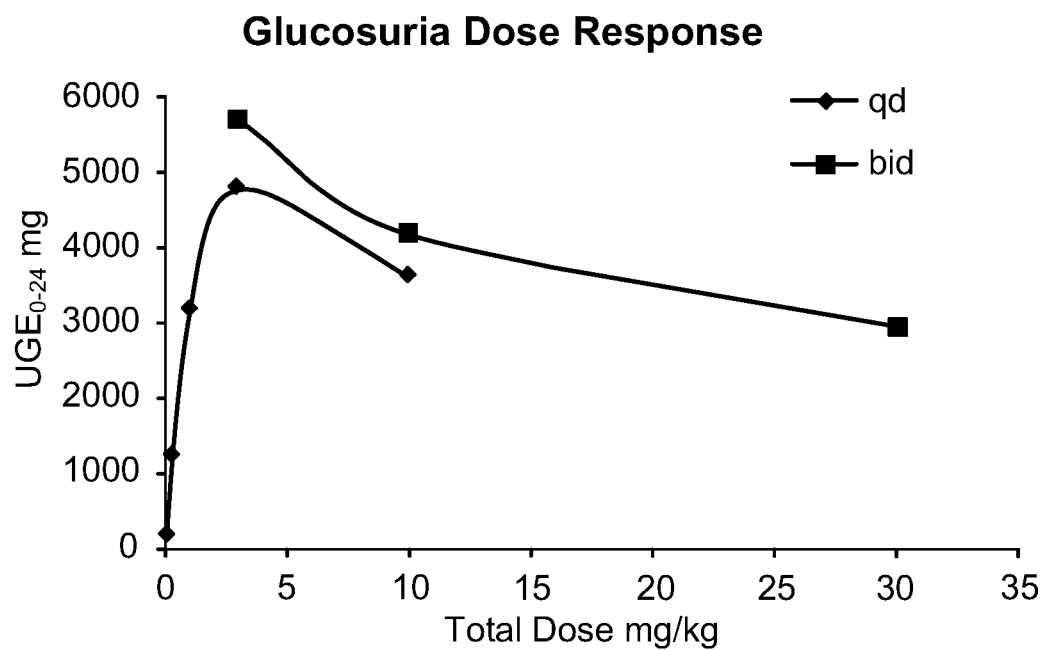
FIG. 5 shows urinary glucose measurements of healthy cats administered bexagliflozin in an inpatient setting.

In studies 1 and 2, bexagliflozin formulated in gelatin capsules was administered to healthy purpose-bred cats and the urinary glucose excretion recorded over the 24-hour period following dosing. Cats were either dosed once (qd) or twice (bid) (in the latter case at 0 and 12 hours). As FIG. 5 shows, the maximum glucosuria was observed at a dose of approximately 3 mg kg$^{-1}$, and dosing twice a day was only slightly more effective than dosing once a day. Cats exposed to the higher quantities of bexagliflozin showed a dose-dependent increase in the severity of loose stools and/or diarrhea, an effect that was consistent with (and attributed to) inhibition of intestinal SGLT1 by the agent. In view of the low in vitro selectivity against feline SGLT2, it appears likely that the pharmacological action of bexagliflozin in cats is the result of inhibition of both SGLT1 and SGLT2.

Because undesired effects attributed to inhibition of SGLT1 were detected at doses 5 to 10 times higher than those producing the maximum pharmacodynamic effect, the potency of bexagliflozin for feline SGLT1 appears nearly optimal. Were the potency against SGLT1 any higher, an overlap between the maximum pharmacodynamic effect and the undesired side effect would ensue.

Figure 6:
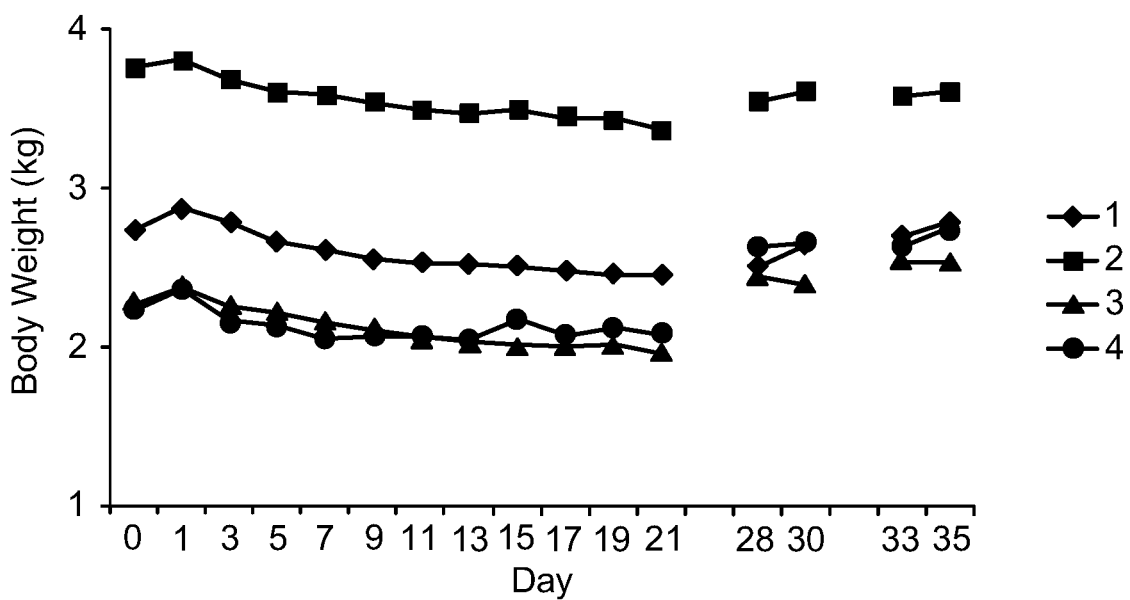
FIG. 6 shows weight loss in healthy cats over time when administered a high daily dose of bexagliflozin.

Further evidence of the desirable potency of bexagliflozin for feline SGLT1 was found in study 3, in which healthy cats were dosed with bexagliflozin 15 mg kg$^{-1}$ bid (30 mg kg$^{-1}$ day$^{-1}$) for 21 days. As FIG. 6 shows, cats lost weight throughout the study, attributed to the caloric wasting due to a combination of glucosuria and diarrhea. All cats regained weight when the dosing ended. Because diabetic cats are often presented as a result of weight loss, the degree of diarrhea would clearly be adverse and incompatible with treatment. Hence a dose ten times higher than that producing the maximum pharmacodynamic effect cannot be sustained. Fortuitously, the effect of bexagliflozin on SGLT1 is not so great as to cause diarrhea at the dose producing the maximum pharmacodynamic effect, but is nonetheless substantial enough to provide clear evidence of consequential enteric inhibition at relatively low multiples of the maximum effective dose.

Example 5. Effects of bexagliflozin in Diabetic Cats

In a field effectiveness study, client-owned cats that had been diagnosed with diabetes mellitus based on: i) two separate fasting (≥6 h) blood glucose measurements>250 mg dL$^{-1}$; ii) glucosuria; iii) fructosamine>450 µmol L$^{-1}$ (subsequently changed to >360 µmol L$^{-1}$ due to a change in the testing laboratory methodology), and iv) one or more of the following: polyuria/polydipsia, polyphagia and/or weight loss (documented in the cat's medical records) were enrolled. Cats with suspected diabetes mellitus were evaluated during visit 1 (within 7 days prior to day 0). Eligible cats were enrolled during visit 2 (day 0) and management was initiated using bexagliflozin administered orally once daily. Cats were prescribed a diet for diabetic animals (Purina DM, either dry or wet variety). Cats were returned to the clinic for evaluation of glycemic control during visits 3 (day 14±3), 4 (day 28±3), and 5 (day 56±3). The treatment period was from visit 2 (day 0) through visit 5 (day 56±3). A cat could have been brought back to the clinic at any time for unscheduled visits if such visits were determined to be necessary by the owner or investigator. Eight-hour blood glucose curves (blood samples collected every 2 h±15 min for 8 h) were conducted at every visit starting with visit 2 (day 0) and blood glucose was measured using an Alpha-TRAK 2 glucometer (Abbott Laboratories). Blood samples for hematology and serum chemistry were collected at screening and during each scheduled visit after initiation of dosing. A central laboratory was used to evaluate all clinical pathology samples (blood, serum, and urine) that are not analyzed in the clinic for blood glucose curves.

Serum chemistries included assessment of fructosamine. A change in measurement methodology at the central laboratory resulted in a shift in the upper limit of normal (ULN) from 356 µmol L$^{-1}$ to 275 µmol L$^{-1}$ during the course of the study. To accommodate the change in reference range, data were harmonized by expression as a percentage of the upper limit of normal and log-transformed percentages were analyzed by repeated measures ANCOVA with an unstructured covariance and visit as a fixed effect. The upper limit of normal for the testing laboratory for fasting serum glucose was 155 mg dL$^{-1}$. The data below were tabulated after 32 cats completed the day 56 visit.

Cats exposed to bexagliflozin in this study were perceived by their owners to have shown improvement in polydipsia, polyphagia and polyuria. Of the three owner-evaluated signs, polyphagia was the least likely to have been found to be improved. Weight gain, despite the caloric wasting induced by bexagliflozin, was also frequently observed.

Strikingly good glycemic control was evident by the measure of serum fructosamine normalization. Of the 32 cats completing the study, 26 achieved a fructosamine concentration that was below the upper limit of normal of the reference laboratory testing range. None of the cats exhibited a symptomatic hypoglycemia, consistent with results of studies of healthy animals that have shown that bexagliflozin at high multiples of the intended clinical dose does not produce hypoglycemia. Freedom from hypoglycemia is also predicted by findings that mice and humans genetically deficient for SGLT2 are euglycemic.

Three cats exhibited elevated serum insulin-like growth factor-1 (IGF-1) and the potential contribution of acromegaly to the etiology of their disease was considered plausible in light of the known association of acromegaly with insulin resistance and insulin-refractory diabetes. All three cats with elevated IGF-1 achieved a normal fructosamine concentration and completed the study as well as a four-month safety assessment extension period. Acromegaly was subsequently confirmed in the cat with the highest IGF-1 concentration. After completion of the study the cat required 11 units of insulin daily and fared poorly clinically.

Improvements in owner-rated or veterinarian-rated measures of cat health or physical condition were recorded, with many of the changes achieving statistical significance. Ketonemia, if apparent at presentation, was typically corrected over the course of the study. A validated survey instrument designed to measure the impact of feline diabetes mellitus on owner quality of life was adapted for the study and a statistically significant improvement in owner life quality was detected.

Detailed Study Outcomes

Each cat was classified as having achieved (or not achieved) glycemic control on Day 56±3 (success/failure). Treatment success was defined as improvement of at least one blood glucose variable (BG mean<250 mg dL$^{-1}$; or fructosamine<450 µmol/L or <360 µmol/L, depending on the assay reference range at the time of the analysis), and the veterinarian's assessment of adequate glycemic control at the final evaluation. Thirty-two of the 40 cats enrolled were considered treatment successes (80%) as shown in Table 3. All cats that remained on-study to V5 were considered treatment successes. Of the 8 cats that were considered treatment failures, 6 cats were removed from the study following an SAE, 1 cat was removed at the sponsor's request, and 1 cat was removed due to the use of a study-proscribed medication to treat an AE. Table 3 also tallies the cats achieving a fructosamine concentration less than the upper limit of normal (356 µmol L$^{-1}$ initially and 275 µmol L$^{-1}$ subsequently).

TABLE 3

Treatment Success Evaluation

| Case | V5 Fructosamine (mmol/L) | V5 Fructosamine Criteria Met | Fructosamine Normal | V5 Mean BG (mg dL$^{-1}$) | Mean BG Criteria Met | V5 Veterinarian Rating of Glycemic Control | V5 Veterinarian Glycemic Control Criteria Met[1] | Treatment Success |
|---|---|---|---|---|---|---|---|---|
| 1 | | | Not Applicable; Cat Removed from Study Prior to V5 | | | | | No |
| 2 | | | Not Applicable; Cat Removed from Study Prior to V5 | | | | | No |
| 3 | 257 | Yes | Yes | 105 | Yes | Excellent | Yes | Yes |
| 4 | 295 | Yes | Yes | 203 | Yes | Good | Yes | Yes |
| 5 | 263 | Yes | Yes | 96 | Yes | Excellent | Yes | Yes |
| 6 | 431 | No | No | 232 | Yes | Good | Yes | Yes |
| 7 | 238 | Yes | Yes | 109 | Yes | Good | Yes | Yes |
| 8 | 329 | Yes | Yes | 136 | Yes | Good | Yes | Yes |
| 9 | 448 | Yes | No | 181 | Yes | Fair | Yes | Yes |
| 10 | 309 | Yes | Yes | 123 | Yes | Fair | Yes | Yes |
| 11 | | | Not Applicable; Cat Removed from Study Prior to V5 | | | | | No |
| 12 | 387 | Yes | No | 109 | Yes | Good | Yes | Yes |
| 13 | 294 | Yes | Yes | 88 | Yes | Good | Yes | Yes |
| 14 | 284 | Yes | Yes | 113 | Yes | Good | Yes | Yes |
| 15 | 302 | Yes | No | 162 | Yes | Fair | Yes | Yes |
| 16 | | | Not Applicable; Cat Removed from Study Prior to V5 | | | | | No |
| 17 | 306 | Yes | No | 60 | Yes | Fair | Yes | Yes |
| 18 | 250 | Yes | Yes | 77 | Yes | Excellent | Yes | Yes |
| 19 | 249 | Yes | Yes | 115 | Yes | Good | Yes | Yes |
| 20 | 272 | Yes | Yes | 102 | Yes | Good | Yes | Yes |
| 21 | 263 | Yes | Yes | 129 | Yes | Good | Yes | Yes |
| 22 | 261 | Yes | Yes | 84 | Yes | Good | Yes | Yes |
| 23 | 320 | Yes | Yes | 139 | Yes | Good | Yes | Yes |
| 24 | | | Not Applicable; Cat Removed from Study Prior to V5 | | | | | No |
| 25 | 256 | Yes | Yes | 100 | Yes | Fair | Yes | Yes |
| 26 | 282 | Yes | Yes | 157 | Yes | Good | Yes | Yes |
| 27 | 235 | Yes | Yes | 103 | Yes | Excellent | Yes | Yes |
| 28 | 282 | Yes | Yes | 128 | Yes | Good | Yes | Yes |
| 29 | 363 | Yes | No | 161 | Yes | Fair | Yes | Yes |
| 30 | 335 | Yes | Yes | 142 | Yes | Good | Yes | Yes |
| 31 | | | Not Applicable; Cat Removed from Study Prior to V5 | | | | | No |
| 32 | | | Not Applicable; Cat Removed from Study Prior to V5 | | | | | No |
| 33 | 220 | Yes | Yes | 100 | Yes | Good | Yes | Yes |
| 34 | 247 | Yes | Yes | 121 | Yes | Good | Yes | Yes |
| 35 | 200 | Yes | Yes | 103 | Yes | Fair | Yes | Yes |
| 36 | 322 | Yes | Yes | 93 | Yes | Good | Yes | Yes |
| 37 | | | Not Applicable; Cat Removed from Study Prior to V5 | | | | | No |
| 38 | 217 | Yes | Yes | 94 | Yes | Good | Yes | Yes |
| 39 | 270 | Yes | Yes | 124 | Yes | Good | Yes | Yes |
| 40 | 226 | Yes | Yes | 97 | Yes | Fair | Yes | Yes |

The clinical signs of acute diabetes mellitus in cats include weight loss, polyuria, polydipsia and polyphagia. All are considered secondary to caloric wasting due to glucosuria, which manifests after the plasma glucose concentration exceeds the renal threshold for glucosuria. Because bexagliflozin reduces the renal threshold for glucosuria, it is expected to exacerbate the clinical signs of hyperglycemia. However, if bexagliflozin were to elevate glucosuria to the extent that a significant reduction of plasma glucose concentration could be achieved, the net effect could be to reduce the total glomerular glucose flux once the plasma glucose concentration normalized. Following normalization, the severity of the clinical signs of hyperglycemia might be reduced. Data collected from the study cohort indicate that the latter effect may be present.

Responsibility for assessing clinical signs of diabetes mellitus was divided between owners and treating veterinarians. Weight was recorded at each visit by the veterinarian, and the signs of polydipsia, polyuria and polyphagia were recorded at each visit by the owner, using a four-point (0 to 3) integer score in which low scores represented favorable ratings.

In addition to providing a measure of the status of the cat as a function of time, the quantitative assessments were used to produce a binary outcome of success or failure at study completion. To score as a success by weight, the weight at Visit 5 was to exceed the weight at Visit 2 (treatment initiation). To score as success by the other signs the owner score at visit 5 was to be less than the owner score at Visit 2.

Table 4 presents the binary outcomes for each cat from the quantitative assessments. Any cat that was withdrawn from the study was scored as a failure (0) in all categories. The last row of Table 4 gives the sum for each column, or the total number of successes by the column criterion. An improvement in at least one of the clinical signs (column 'Any Success') was observed for 31 cats, one fewer than were found to have achieved glycemic control. Case 5 was a glycemic success but a clinical sign failure. For this cat the owner scores were identical for all visits for each category, and the weight decreased from 5.4 kg to 5.1 kg. Excluding weight as a criterion (column 'Non-Weight Success') 30 cats were scored as successes. The additional cat failing by non-weight criteria was case 4. For this cat the final and initial scores in each category were identical. However, the cats of both case 4 and 5 were rated by their owners as having shown improvement in polydipsia, polyuria or polyphagia when qualitatively compared to study initiation, as discussed in the following section.

TABLE 4

Binary Success Outcomes for Quantitative Assessments of Clinical Signs

| Case | Weight Success | Polydipsia Success | Polyuria Success | Polyphagia Success | Any Success | Non-Weight Success |
|---|---|---|---|---|---|---|
| 1 | 0 | 0 | 0 | 0 | 0 | 0 |
| 2 | 0 | 0 | 0 | 0 | 0 | 0 |
| 3 | 0 | 1 | 1 | 0 | 1 | 1 |
| 4 | 1 | 0 | 0 | 0 | 1 | 0 |
| 5 | 0 | 0 | 0 | 0 | 0 | 0 |
| 6 | 1 | 1 | 0 | 1 | 1 | 1 |
| 7 | 1 | 0 | 0 | 1 | 1 | 1 |
| 8 | 1 | 1 | 1 | 0 | 1 | 1 |
| 9 | 0 | 1 | 1 | 1 | 1 | 1 |
| 10 | 1 | 1 | 1 | 1 | 1 | 1 |
| 11 | 0 | 0 | 0 | 0 | 0 | 0 |
| 12 | 1 | 0 | 1 | 0 | 1 | 1 |
| 13 | 1 | 1 | 1 | 1 | 1 | 1 |
| 14 | 1 | 0 | 1 | 0 | 1 | 1 |
| 15 | 1 | 1 | 1 | 0 | 1 | 1 |
| 16 | 0 | 0 | 0 | 0 | 0 | 0 |
| 17 | 1 | 1 | 0 | 0 | 1 | 1 |
| 18 | 1 | 1 | 1 | 1 | 1 | 1 |
| 19 | 1 | 0 | 1 | 1 | 1 | 1 |
| 20 | 1 | 1 | 1 | 1 | 1 | 1 |
| 21 | 1 | 1 | 1 | 1 | 1 | 1 |
| 22 | 0 | 1 | 1 | 1 | 1 | 1 |
| 23 | 1 | 0 | 1 | 0 | 1 | 1 |
| 24 | 0 | 0 | 0 | 0 | 0 | 0 |
| 25 | 0 | 1 | 1 | 0 | 1 | 1 |
| 26 | 0 | 1 | 1 | 0 | 1 | 1 |
| 27 | 1 | 0 | 1 | 1 | 1 | 1 |
| 28 | 0 | 1 | 0 | 0 | 1 | 1 |
| 29 | 0 | 0 | 0 | 1 | 1 | 1 |
| 30 | 1 | 1 | 1 | 1 | 1 | 1 |
| 31 | 0 | 0 | 0 | 0 | 0 | 0 |
| 32 | 0 | 0 | 0 | 0 | 0 | 0 |
| 33 | 1 | 0 | 1 | 0 | 1 | 1 |
| 34 | 1 | 1 | 1 | 1 | 1 | 1 |
| 35 | 1 | 1 | 1 | 0 | 1 | 1 |
| 36 | 1 | 1 | 1 | 0 | 1 | 1 |
| 37 | 0 | 0 | 0 | 0 | 0 | 0 |
| 38 | 0 | 1 | 1 | 1 | 1 | 1 |
| 39 | 1 | 1 | 1 | 1 | 1 | 1 |
| 40 | 0 | 1 | 1 | 1 | 1 | 1 |
| Col Sum | 22 | 23 | 24 | 17 | 31 | 30 |

Figure 7:
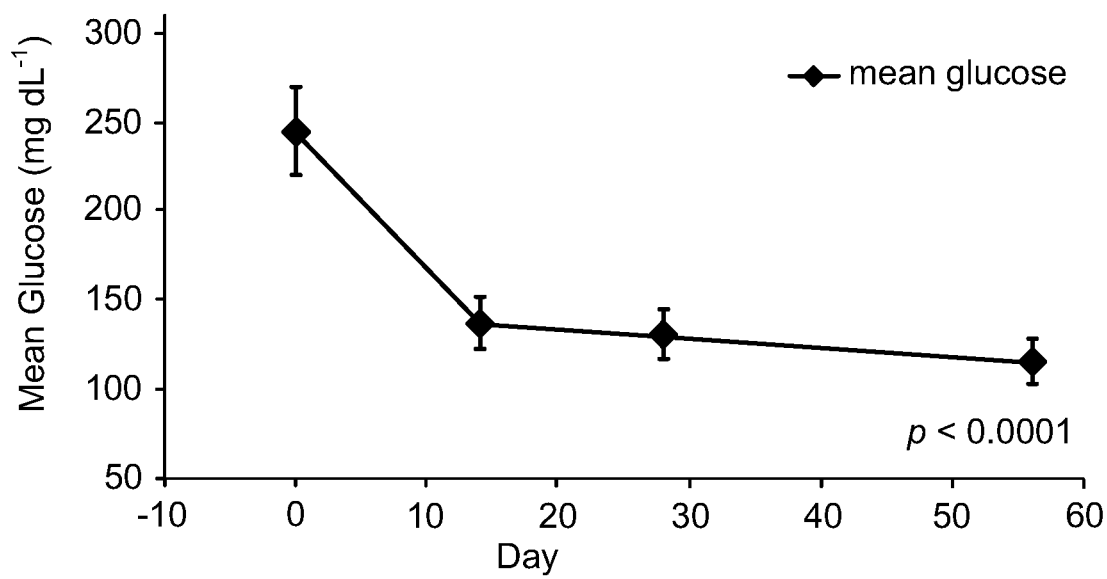
FIG. 7 shows model-adjusted least squares means of the five in-clinic blood glucose curve measurements for each curve by visit over 8 hours, with 95% confidence intervals. The mean blood glucose concentration observed in the clinic decreased with duration of treatment by a statistically highly significant extent.
Figure 8:
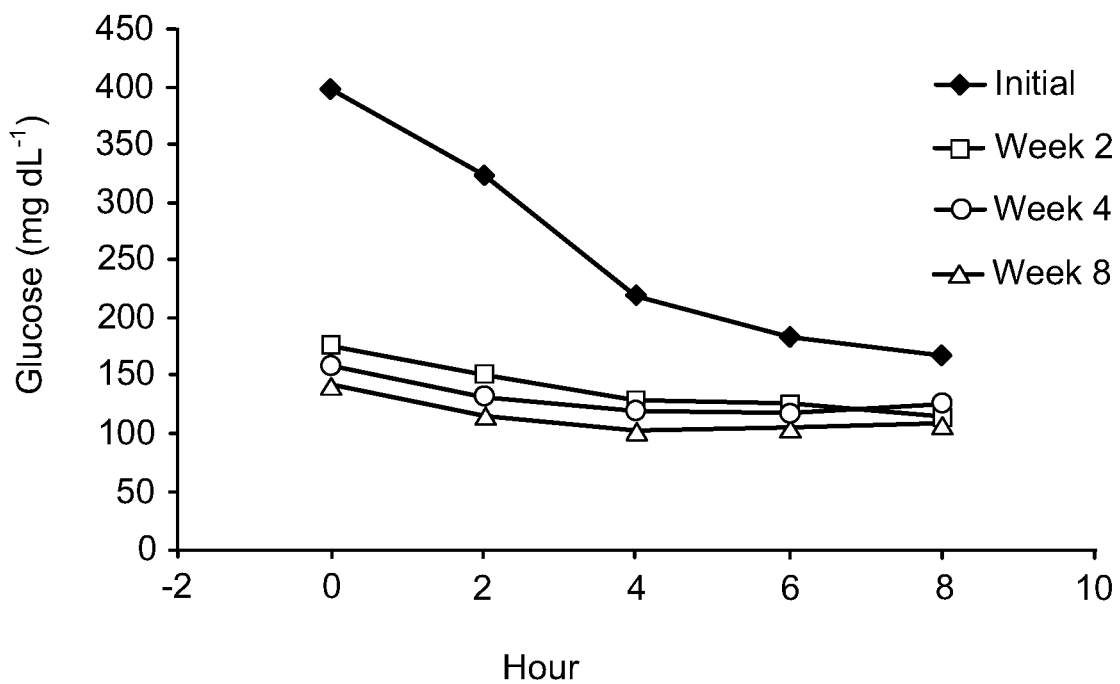
FIG. 8 shows the mean values for the individual measurements making up the blood glucose curves, by visit as a function of sampling time. After the initial measurement, the blood glucose curves differed little from visit to visit. At week 8, the mean of the five blood glucose determinations was 114.9 mg dL$^{-1}$ (95% CI 102.8, 128.4).

Glucose curves were constructed by glucometer measurement of blood sampled at hours 0, 2, 4, 6 and 8 post-dose. Log-transformed data were analyzed in by a mixed model repeated measures ANCOVA with a first order autoregressive covariance structure and taking visit, hour and visit by hour as fixed effects and hour as a random effect. FIG. 7 below displays model-adjusted least squares means of the five measurements for each curve by visit, with 95% confidence intervals. Mean data for individual visits (second plot below) were analyzed by repeated measures ANCOVA with hour as a fixed effect and a first order autoregressive covariance structure. Data from the 40 enrolled cats is shown in FIG. 8. At week 8 the mean of the five blood glucose determinations was 114.9 mg dL$^{-1}$ (95% CI 102.8, 128.4).

Figure 9:
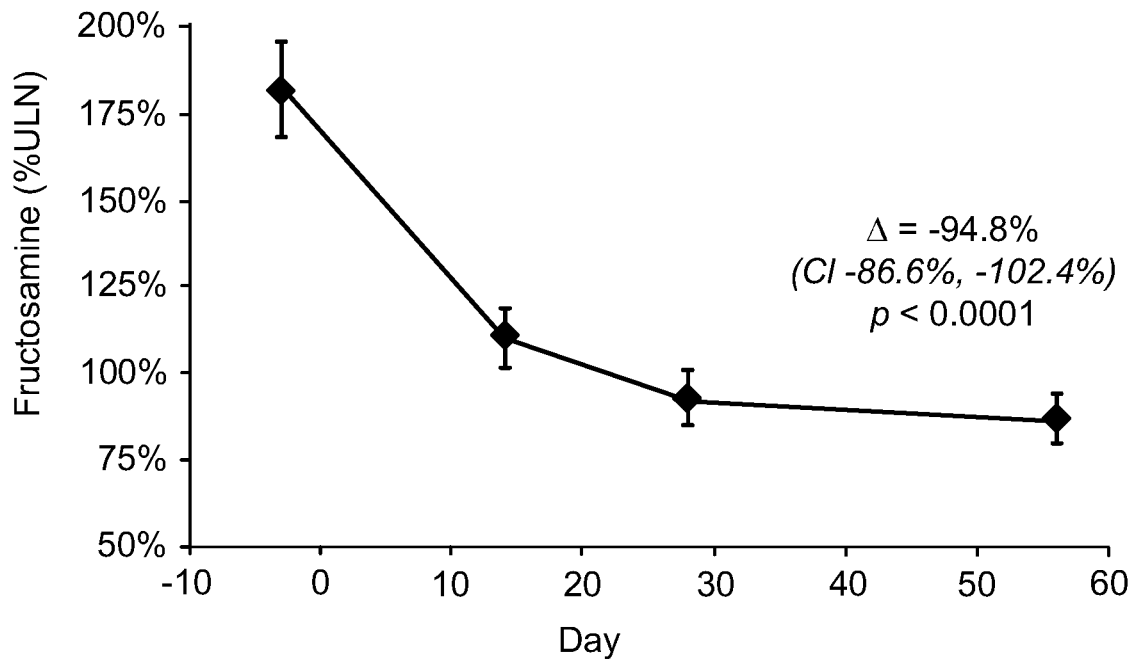
FIG. 9 shows the mean values for cat serum fructosamine by visit. The graph shows model-adjusted least squares means with 95% confidence intervals. The inset value Δ represents the least squares mean difference from baseline to week 8 expressed as a percent of the upper limit of normal with the corresponding 95% confidence interval. At week 8 the mean serum fructosamine of the population was 86.7% of the upper limit of normal (95% CI 80.0%, 93.9%) and the change in fructosamine concentration was highly significant.

Serum fructosamine concentration was measured by the central lab at screening (V1) and at each visit post enrollment (V3, V4, and V5). A change in measurement methodology at the central laboratory resulted in a shift in the upper limit of normal (ULN) from 356 μmol L$^{-1}$ to 275 μmol L$^{-1}$. Data were harmonized by expression as a percentage of the upper limit of normal and log-transformed percentages were analyzed by repeated measures ANCOVA with an unstructured covariance and visit as a fixed effect. FIG. 9 displays model-adjusted least squares means with 95% confidence intervals. The inset value Δ represents the least squares mean difference from baseline to week 8 expressed as a percent of ULN with the corresponding 95% confidence interval. At week 8 the mean serum fructosamine of the population was 86.7% of the upper limit of normal (95% CI 80.0%, 93.9%).

Figure 10:
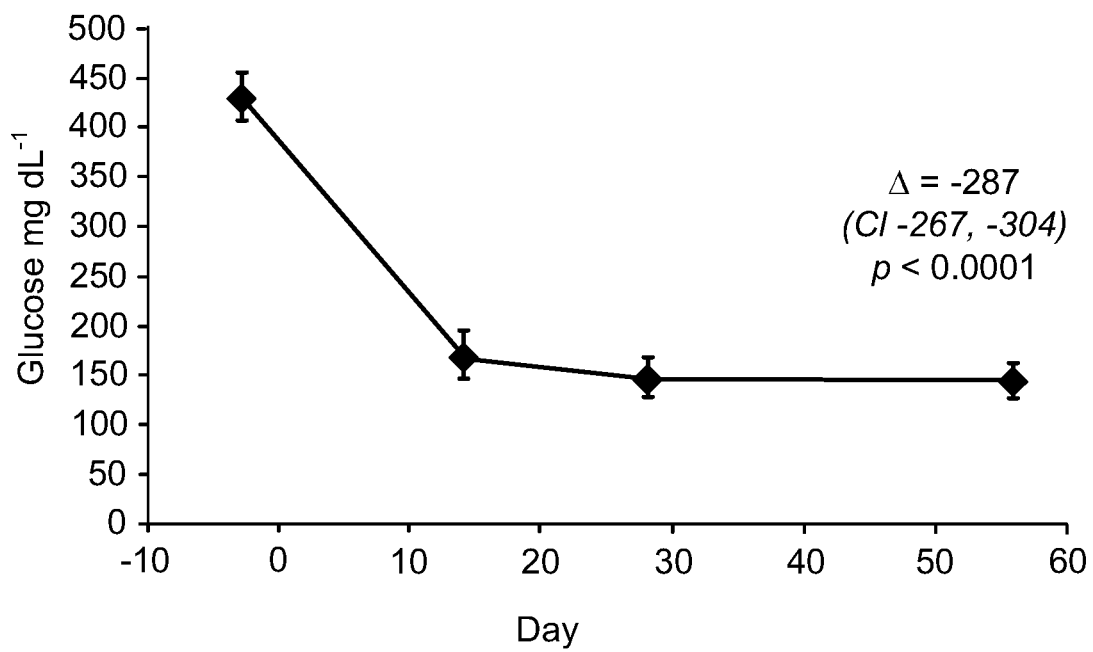
FIG. 10 displays model-adjusted least squares means of the cat serum glucose concentrations with 95% confidence intervals. The inset text gives the least squares mean difference from baseline to week 8 with the corresponding 95% confidence interval. At week 8 the mean serum glucose was 144 (95% CI 127, 163) and the change in serum glucose concentration was highly significant.

Serum glucose concentration was measured by the central lab at screening (V1) and at each visit post enrollment (V3, V4, and V5). Log-transformed data were analyzed by repeated measures ANCOVA with an unstructured covariance and visit as a fixed effect. FIG. 10 displays model-adjusted least squares means with 95% confidence intervals. The inset text gives the least squares mean difference from baseline to week 8 with the corresponding 95% confidence interval. At week 8 the mean serum glucose was 144 (95% CI 127, 163).

Figure 11:
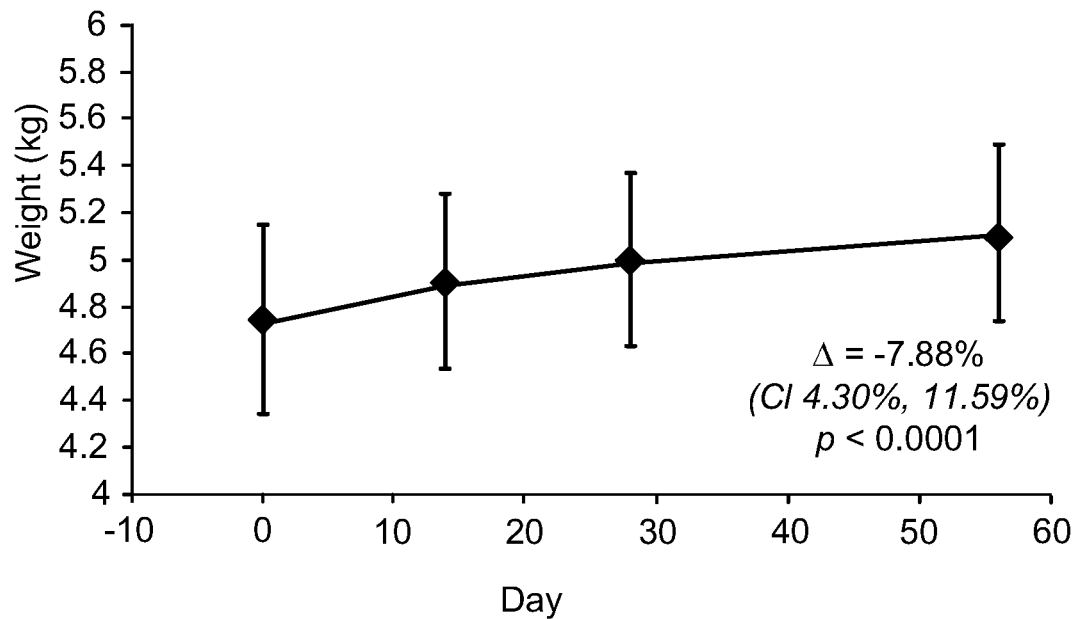
FIG. 11 shows model-adjusted least squares mean cat body mass by visit, with 95% confidence intervals. The inset gives the least squares mean difference from baseline to week 8 as a percent of initial weight, with 95% confidence interval. Although the confidence intervals are wide because the population is heterogeneous with respect to weight, the treatment effect on the gain in body mass per cat was highly significant.

Cats often entered the study because their owners observed that they were losing weight, despite consuming more food than usual. As FIG. 11 shows, the average cat weight increased over the course of the study. By day 56, 82% of the cats had either maintained or increased their weight, and none of the cats had lost more than 5% of their weight from study entry.

Weight was measured at each study visit. Log-transformed data were analyzed as above. FIG. 11 displays model-adjusted least squares means with 95% confidence intervals. The inset gives the least squares mean difference from baseline to week 8 as a percent of initial weight, with 95% confidence interval. Although the confidence intervals are wide because the population is heterogeneous with respect to weight at study entry, the treatment effect on the gain in body mass per cat was highly significant (p<0.0001). The weight gain effect is striking and runs counter to the expectation that the caloric wasting due to bexagliflozin-induced glucosuria would lead to a decrease in cat weight.

Figure 12:
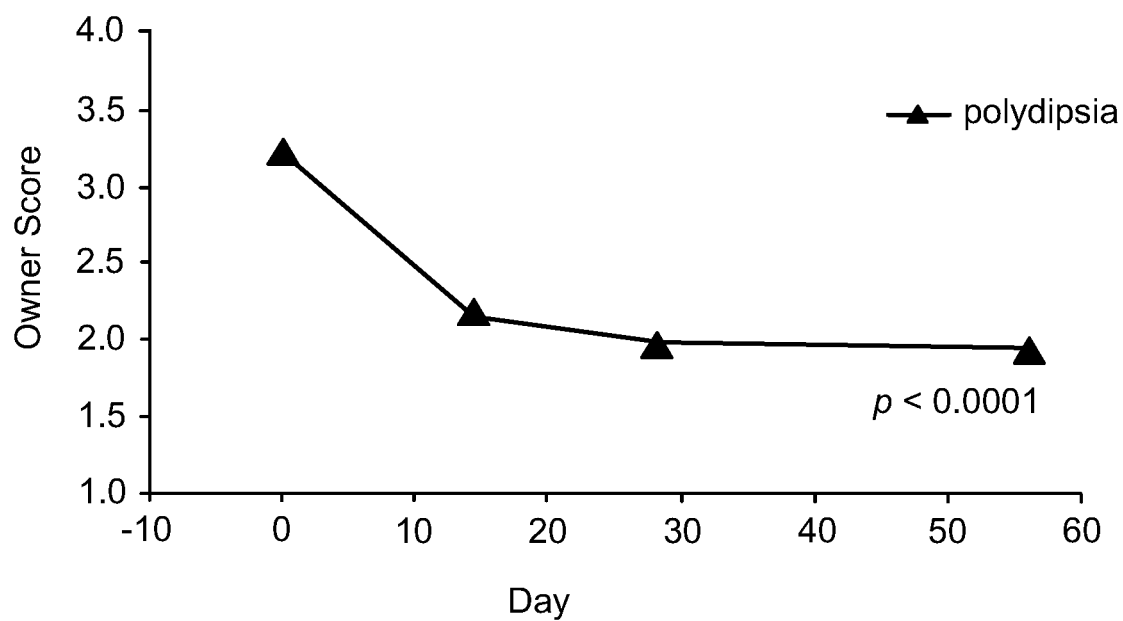
FIG. 12 shows the mean owner scores for polydipsia (excessive drinking) declined by visit. The data were not normally distributed but a non-parametric test (indicating significant difference between values, but not identifying a specific pair) was highly significant.
Figure 13:
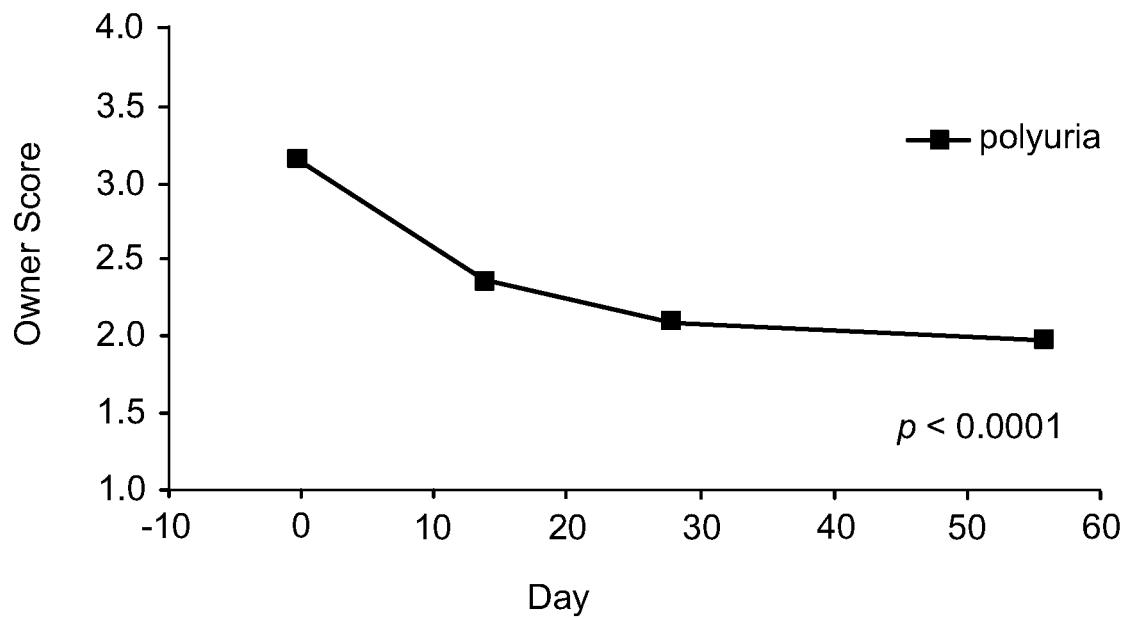
FIG. 13 shows the mean owner scores for polyuria (excessive urination) declined by visit. The data were not normally distributed but a non-parametric test (indicating significant difference between values, but not identifying a specific pair) was highly significant.
Figure 14:
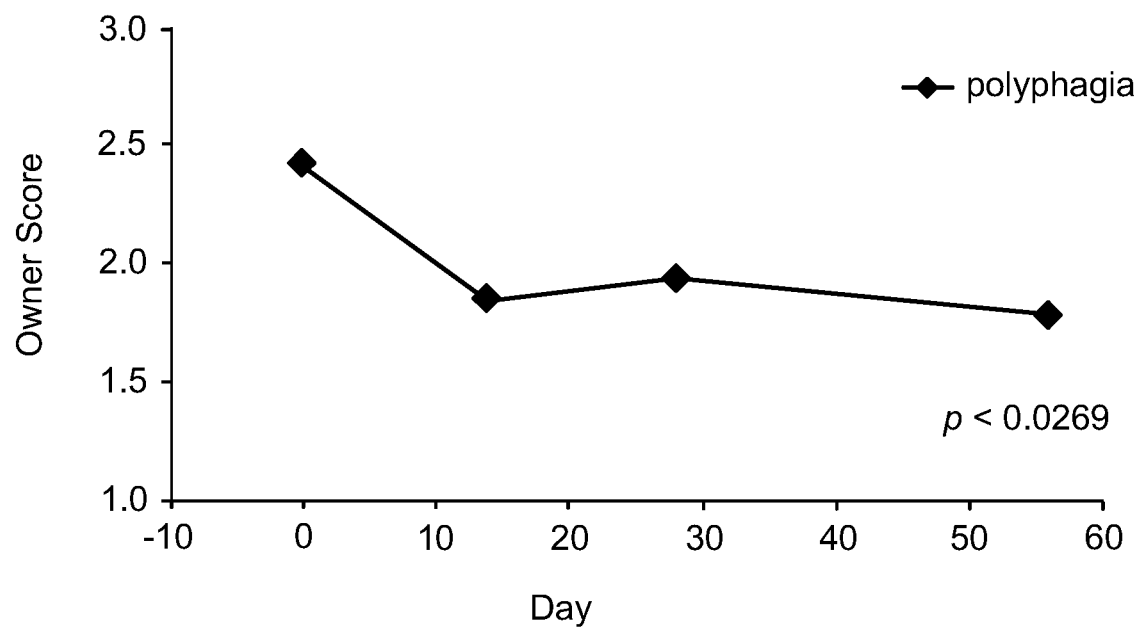
FIG. 14 shows the mean owner scores for polyphagia (excessive eating) declined by visit. The data were not normally distributed but a non-parametric test (indicating significant difference between values, but not identifying a specific pair) was significant.

Throughout the study, owners were asked to provide assessments of their cats' hyperglycemia-associated clinical signs according to a four-point qualitative score in which 0 represented excellent and 3 represented poor. Separate assessments were recorded for polyphagia, polydipsia and polyuria. Significant differences were detected for all three measures (FIGS. 12, 13 and 14), with the smallest magnitude of effect apparent for owner-assessed polyphagia. Despite the owners' perceptions that their cats were exhibiting reduced signs of polyphagia, the objective weights of their cats increased. Thus, even though the mechanism of action of bexagliflozin involves caloric wasting through glucosuria, the effect on hyperglycemia-associated clinical signs was more profound than the effect of the caloric loss induced by bexagliflozin.

Acromegaly-associated diabetes in cats represents a distinct etiology with particular challenges for management. Very high insulin doses are often required to overcome the profound insulin resistance typically encountered in such cases. In addition to the morphological changes that accompany disease of longstanding duration, elevated IGF-1 concentrations are pathognomonic for acromegaly in cats. Three cats entered the study with IGF-1 concentrations above the upper limit of normal (92 nmol/L): case 7 (172 nmol/L), case 28 (100 nmol/L) and case 30 (120 nmol/L). All three cases were considered treatment successes at V5 and completed the extended safety study for a total of 6 months of treatment.

Figure 15:
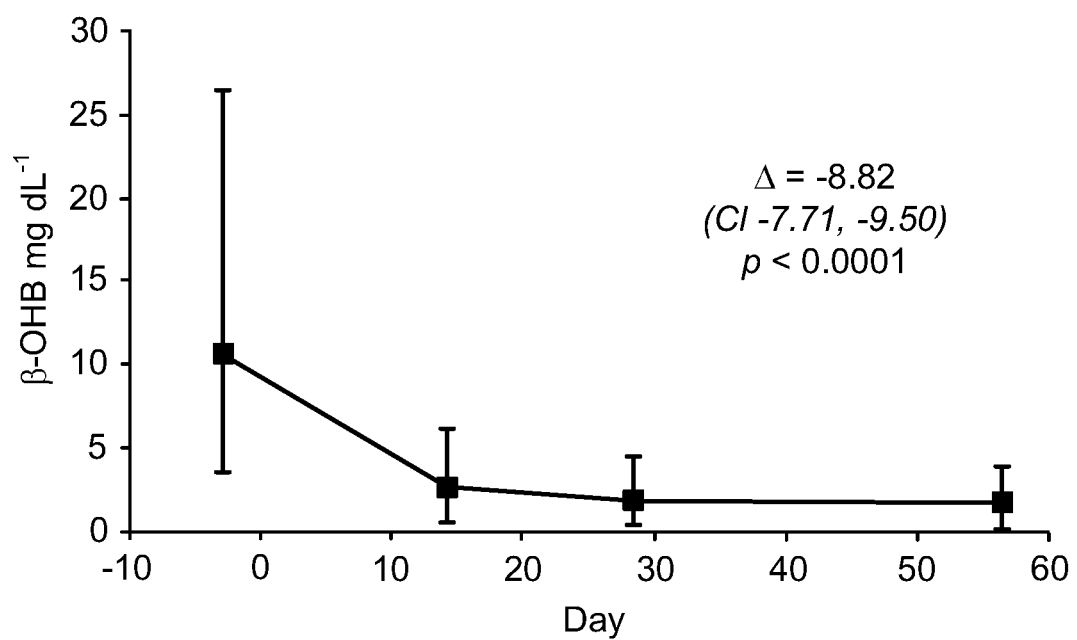
FIG. 15 shows the mean serum β-hydroxybutyrate concentration with 95% confidence intervals, by visit. The wide margins for the first visit reflect the great range in values among cats entering the study. At week 8 the mean serum β-hydroxybutyrate concentration was 1.76 mg dL$^{-1}$ (95% CI 1.40, 2.20), lower than the upper limit of normal for the testing laboratory (1.9 mg dL$^{-1}$) and the change from study entry was highly significant.

Ketonemia and ketoacidosis are two manifestations of a severe loss of glycemic control. As the available insulin fails to result in sufficient reduction in plasma glucose, a ketosis results from the failure of adipocytes to fully assimilate the glucose burden. The most reliable analyte for the measurement of ketonemia is β-hydroxybutyrate. Serum β-hydroxybutyrate (β-OHB) concentration was measured by the central lab at screening (VI) and at each visit post enrollment (V3, V4, and V5). Log-transformed data were analyzed by mixed model repeated measures ANCOVA with an unstructured covariance and visit as a fixed effect. FIG. 15 displays model-adjusted least squares means with 95% confidence intervals. The inset text gives the least squares mean difference from baseline to week 8 with the corresponding 95% confidence interval. At week 8 the mean serum β-hydroxybutyrate concentration was 1.76 mg dL$^{-1}$ (95% CI 1.40, 2.20), lower than the upper limit of normal for the testing laboratory (1.9 mg dL$^{-1}$). The very large confidence interval for the values for the initial visit reflect the extreme variation observed in the degree of ketonemia exhibited by cats at study entry.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of managing diabetes in a cat in need thereof, said method comprising administering to the cat in need thereof a total daily dosage comprising about 5 to 50 mg of a pharmaceutically acceptable form of Compound 1,

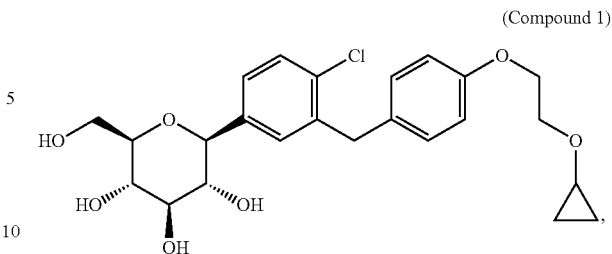

(Compound 1)

wherein administration of said total daily dosage of Compound 1 reduces hyperglycemia-associated clinical signs comprising (a) polydipsia, (b) polyphagia, (c) polyuria, and (d) weight loss, and wherein the pharmaceutically acceptable form of Compound 1 is a crystalline form of Compound 1 characterized by Raman spectra including peaks at about 353, 688 and 825 cm$^{-1}$.

2. The method of claim 1, wherein said total daily dosage is about 10 to 20 mg.

3. The method of claim 1 wherein said total daily dosage is about 15 mg.

4. The method of claim 1, wherein Compound 1 is administered orally.

5. The method of claim 1, wherein Compound 1 is administered once daily.

6. The method of claim 1, wherein the crystalline form of Compound 1 is the only antidiabetic agent administered to said cat.

7. The method of claim 1, wherein administration of the crystalline form of Compound 1 produces clinical remission in said cat.

8. The method of claim 1, wherein the crystalline form of Compound 1 is characterized by Raman spectra substantially in accordance with FIG. 4.

* * * * *